US012757315B2

(12) United States Patent
Hori et al.

(10) Patent No.: US 12,757,315 B2
(45) Date of Patent: Oct. 6, 2026

(54) ACCELERATOR AND PARTICLE THERAPY SYSTEM

(71) Applicant: Hitachi High-Tech Corporation, Tokyo (JP)

(72) Inventors: Chishin Hori, Tokyo (JP); Kento Nishida, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 381 days.

(21) Appl. No.: 18/203,683

(22) Filed: May 31, 2023

(65) Prior Publication Data

US 2024/0023225 A1 Jan. 18, 2024

(30) Foreign Application Priority Data

Jul. 13, 2022 (JP) ................................ 2022-112290

(51) Int. Cl.
*H05H 7/10* (2006.01)
*A61N 5/10* (2006.01)
(Continued)

(52) U.S. Cl.
CPC ................. *H05H 7/10* (2013.01); *A61N 5/10* (2013.01); *H05H 7/04* (2013.01); *H05H 13/02* (2013.01);
(Continued)

(58) Field of Classification Search
CPC ........ H05H 7/10; H05H 13/02; H05H 13/005; H05H 7/04; H05H 2277/11; A61N 5/10; A61N 2005/1087
See application file for complete search history.

(56) References Cited

U.S. PATENT DOCUMENTS 3,624,527 A * 11/1971 Hudson .................... H05H 7/10 313/62
3,896,392 A * 7/1975 Hudson .................... H05H 7/10 313/62
(Continued)

FOREIGN PATENT DOCUMENTS

JP H05258897 A * 10/1993
JP 2019-133745 A 8/2019
(Continued)

OTHER PUBLICATIONS

Office Action received in corresponding Japanese Application No. 2022-112290 dated Dec. 16, 2025.
(Continued)

*Primary Examiner* — Wyatt A Stoffa
(74) *Attorney, Agent, or Firm* — MATTINGLY & MALUR, PC

(57) ABSTRACT

An accelerator includes: a main magnetic field magnet that has a plurality of magnetic poles and excites the main magnetic field in a space interposed between the magnetic poles; a magnetic channel that extracts the ion beam from an inside of the main magnetic field magnet toward an outside of the main magnetic field magnet; a displacement unit that displaces the ion beam circulating in a main magnetic field region to an outer side of the main magnetic field region; and a disturbance magnetic field region that is provided in an outer peripheral portion of the main magnetic field region and excites a magnetic field which disturbs the ion beam displaced to the outer side and guides the ion beam to the magnetic channel, the magnetic channel including a predetermined mechanism that suppresses a magnetic field gradient generated radially inward in the circulating ion beam region.

8 Claims, 17 Drawing Sheets

(51) Int. Cl.
*H05H 7/04* (2006.01)
*H05H 13/02* (2006.01)

(52) U.S. Cl.
CPC .. *A61N 2005/1087* (2013.01); *H05H 2277/11* (2013.01)

(56) References Cited

U.S. PATENT DOCUMENTS

| | | | | |
|---|---|---|---|---|
| 6,683,426 | B1 | 1/2004 | Kleeven | |
| 11,457,523 | B2 * | 9/2022 | Aoki | H05H 13/02 |
| 11,849,533 | B2 * | 12/2023 | Hae | H05H 13/005 |
| 12,370,221 | B2 * | 7/2025 | Eberli | A61K 35/34 |
| 2005/0258784 | A1 * | 11/2005 | Makita | C22C 33/0278 315/502 |
| 2006/0056596 | A1 * | 3/2006 | Mori | H05H 13/08 378/138 |
| 2013/0207001 | A1 * | 8/2013 | Sugahara | H05H 7/10 250/492.1 |
| 2014/0232497 | A1 * | 8/2014 | Sugita | H05H 7/04 335/213 |
| 2017/0339778 | A1 * | 11/2017 | Aoki | H05H 13/04 |
| 2018/0326226 | A1 * | 11/2018 | Ebina | H05H 7/04 |
| 2021/0195725 | A1 * | 6/2021 | Hae | A61N 5/10 |
| 2021/0196984 | A1 * | 7/2021 | Hae | H05H 7/04 |
| 2023/0105721 | A1 * | 4/2023 | Hae | A61N 5/10 315/501 |
| 2024/0198138 | A1 * | 6/2024 | Ebina | A61N 5/10 |

FOREIGN PATENT DOCUMENTS

| | | | |
|---|---|---|---|
| JP | 2019-175682 | A | 10/2019 |
| JP | 2020-38797 | A | 3/2020 |

OTHER PUBLICATIONS

Chinese Office Action received in corresponding Chinese Application No. 202310543847.3 dated Jul. 13, 2026.

* cited by examiner

ACCELERATOR AND PARTICLE THERAPY SYSTEM

CROSS-REFERENCE TO RELATED APPLICATION

The present application claims priority from Japanese application JP2022-112290, filed on Jul. 13, 2022, the contents of which is hereby incorporated by reference into this application.

BACKGROUND OF THE INVENTION

1. Field of the Invention

The present disclosure relates to an accelerator and a particle therapy system.

2. Description of the Related Art

Particle therapy is a type of radiation therapy, and is a treatment method in which a tumor is irradiated with an ion beam, such as a proton beam or a carbon beam, to destroy a cell in the tumor. A particle therapy system configured for implementation of the particle therapy includes: an ion source that generates ions; an accelerator that accelerates the ions generated by the ion source to form an ion beam; a beam transport that transports the ion beam formed by the accelerator from the accelerator to a treatment room; a rotating gantry that changes an irradiation direction of the ion beam transported by the beam transport with respect to a tumor; an irradiation system that irradiates the tumor with the ion beam from the rotating gantry; and a control system that controls these components.

JP 2019-133745 A discloses an accelerator that does not require attenuation of an ion beam on the outside by making an energy of the ion beam to be extracted outside variable in spite of using a static main magnetic field. The accelerator described in JP 2019-133745 A accelerates the ion beam circulating in the accelerator to a desired energy, and then, feeds, to the ion beam, a radiofrequency electric field in a direction (hereinafter, referred to as a horizontal direction) substantially vertical to a traveling direction of the ion beam and a magnetic pole gap direction (hereinafter, a vertical direction) of the main magnetic field. Particles of the ion beam to which the radiofrequency electric field has been fed passes through a magnetic field region, which is called a peeler magnetic field and a regenerator magnetic field and configured to generate a resonance of betatron oscillation formed around a center orbit, with the amplitude in the horizontal direction of the betatron oscillation, which is oscillation around the center orbit, increasing gradually. The ion beam passing through the peeler magnetic field and the regenerator magnetic field rapidly increases in amplitude in the horizontal direction of the betatron oscillation, enters a septum magnetic field for extraction, and is extracted to the outside of the accelerator.

Here, an extraction system structure used to extract the ion beam includes a magnetic channel, a radiofrequency kicker, shims that form the peeler magnetic field and the regenerator magnetic field, and the like. In the magnetic channel, a magnetic field is formed not only in an internal region thereof but also in a circulating beam region, and thus, the circulating beam is made unstable. Therefore, in JP 2019-175682 A, an iron member is arranged on the inner side of a magnetic channel to correct a magnetic field in the vicinity of the magnetic channel.

SUMMARY OF THE INVENTION

When the iron member for magnetic field correction is provided on the inner side of the magnetic channel as in JP 2019-175682 A, the iron member approaches a median plane, so that a width of a beam in the vertical direction is limited, thereby lowering the beam extraction efficiency.

An object of the present disclosure is to provide an accelerator and a particle therapy system capable of improving the ion beam extraction efficiency.

An accelerator according to one aspect of the present disclosure is an accelerator that accelerates an ion beam while circulating the ion beam by a main magnetic field and an accelerating radiofrequency electric field, and includes: a main magnetic field magnet that has a plurality of magnetic poles arranged to face each other and excites the main magnetic field in a space interposed between the magnetic poles; a magnetic channel that extracts the ion beam from an inside of the main magnetic field magnet toward an outside of the main magnetic field magnet; a displacement unit that displaces the ion beam circulating in a main magnetic field region where the main magnetic field is excited to an outer side of the main magnetic field region; and a disturbance magnetic field region that is provided in an outer peripheral portion of the main magnetic field region and excites a magnetic field which disturbs the ion beam displaced to the outer side and guides the ion beam to the magnetic channel, the magnetic channel including a predetermined mechanism that suppresses a magnetic field gradient generated radially inward in the circulating ion beam region.

According to the present disclosure, the magnetic channel can suppress the magnetic field gradient generated on the radially inner side in the circulating ion beam region, and can improve the ion beam extraction efficiency.

DESCRIPTION OF THE PREFERRED EMBODIMENTS

Hereinafter, an embodiment of the present disclosure will be described with reference to the drawings. In the present embodiment, a predetermined mechanism is provided in a magnetic channel to suppress a magnetic field gradient generated on the radially inner side of the magnetic channel in a circulating ion beam region, by the predetermined mechanism. In the present disclosure, a recessed part is provided on the inner side of the magnetic channel (the inner side along the radial direction of a main magnetic field magnet) to generate a leakage magnetic field in the recessed part. The leakage magnetic field generated in the recessed part is opposite to a magnetic field that passes through a septum and returns from the radially inner side, and thus, the magnetic field gradient generated radially inward by the septum can be reduced, and the extraction efficiency of the ion beam can be improved.

Embodiment

Figure 1:
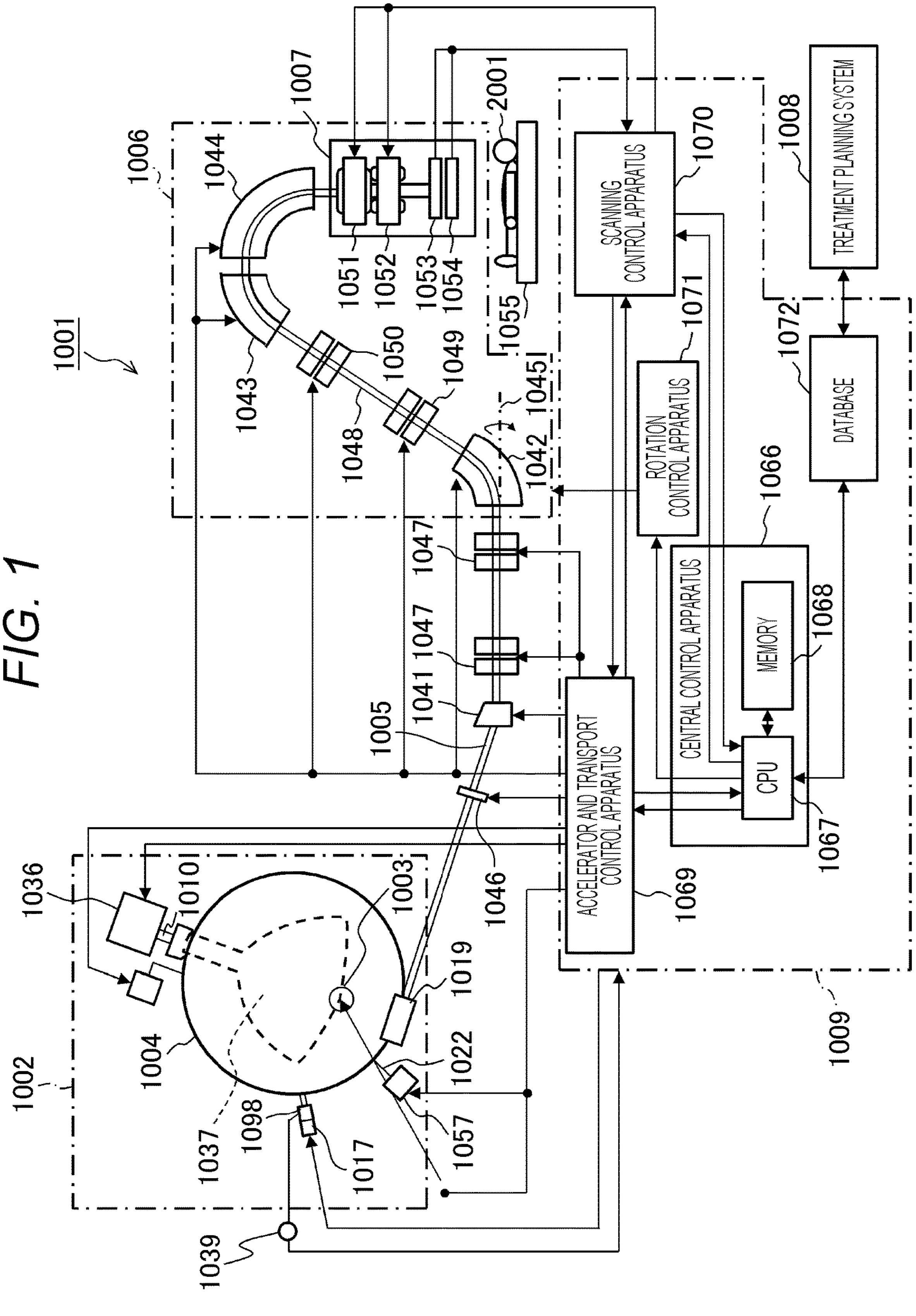
FIG. 1 is a configuration diagram of a particle therapy system according to an embodiment of the present disclosure.

FIG. 1 is a diagram illustrating an overall configuration of a particle therapy system according to the embodiment of the present disclosure. A particle therapy system 1001 illustrated in FIG. 1 is a system that irradiates a subject with an ion beam formed by accelerating ions by an accelerator 1004 to be described later. The accelerator 1004 of the present embodiment accelerates an ion beam using hydrogen ions as ions, that is, protons, to any energy within a predetermined range and extracts the accelerated ion beam. The predetermined range is a range from 70 MeV to 235 MeV in the present embodiment. The ion beam may be a heavy particle ion beam using helium, carbon, or the like, and an extraction energy, which is an energy of an ion beam to be extracted, is not limited to the range of 70 MeV to 235 MeV.

The particle therapy system 1001 illustrated in FIG. 1 is installed on a floor surface of a building (not illustrated). The particle therapy system 1001 includes an ion beam generator 1002, a beam transport 1005, a rotating gantry 1006, an irradiation system 1007, a treatment planning system 1008, and a control system 1009. The ion beam generator 1002 includes an ion source 1003 and the accelerator 1004.

The ion source 1003 is an ion introduction system that supplies ions to the accelerator 1004. The accelerator 1004 accelerates the ions supplied from the ion source 1003 to form an ion beam, and extracts the ion beam. The accelerator 1004 is connected with a radiofrequency power supply 1036, which is a power supply of a radiofrequency acceleration cavity 1037, and a coil excitation power supply 1057. The accelerator 1004 is connected with an ion beam current measurement system 1098 that measures a current of the ion beam. The ion beam current measurement system 1098 includes a moving system 1017 and a position detector 1039. A more detailed description of the accelerator 1004 will be described later.

The beam transport 1005 is a transport line that transports the ion beam extracted from the accelerator 1004 to the irradiation system 1007, and has an ion beam path 1048 through which the ion beam passes. The ion beam path 1048 is connected to a magnetic channel 1019, configured to extract the ion beam from the accelerator 1004, and the irradiation system 1007. In the ion beam path 1048, magnets, configured to transport the ion beam from the accelerator 1004 toward the irradiation system 1007, are arranged in the order of a plurality of quadrupole magnets 1046, a bending magnet 1041, a plurality of quadrupole magnets 1047, a bending magnet 1042, a quadrupole magnet 1049, a quadrupole magnet 1050, a bending magnet 1043, and a bending magnet 1044.

The rotating gantry 1006 is configured to be rotatable about a rotation axis 1045, and is a rotating system that rotates the irradiation system 1007 around the rotation axis 1045. A part of the ion beam path 1048 is installed in the rotating gantry 1006. Among the magnets configured to transport the ion beam, the bending magnet 1042, the quadrupole magnets 1049 and 1050, and the bending magnets 1043 and 1044 are installed in the rotating gantry 1006.

The irradiation system 1007 is attached to the rotating gantry 1006 and is connected to the ion beam path 1048 on the downstream side of the bending magnet 1044.

The irradiation system 1007 includes scanning magnets 1051 and 1052, a beam position monitor 1053, and a dose monitor 1054. The scanning magnets 1051 and 1052, the beam position monitor 1053, and the dose monitor 1054 are arranged in a casing (not illustrated) of the irradiation system 1007. The scanning magnets 1051 and 1052, the beam position monitor 1053, and the dose monitor 1054 are arranged along a central axis of the irradiation system 1007, that is, a beam axis of the ion beam.

The scanning magnet 1051 and the scanning magnet 1052 respectively constitute scanning systems that bend the ion beam and scan the ion beams in directions substantially orthogonal to each other in a plane substantially vertical to the central axis of the irradiation system 1007. The beam position monitor 1053 and the dose monitor 1054 are arranged downstream of the scanning magnets 1051 and 1052. The beam position monitor 1053 measures a passage position of the ion beam. The dose monitor 1054 measures a dose of the ion beam.

On the downstream side of the irradiation system 1007, a treatment table 1055 on which a patient 2001 as the subject lies is arranged to face the irradiation system 1007.

The treatment planning system 1008 generates an irradiation content of the ion beam for the patient 2001 as treatment planning and notifies the control system 1009 of the treatment planning. The irradiation content includes, for example, an irradiation region, an irradiation energy, an irradiation angle, the number of times of irradiation, and the like of the ion beam.

The control system 1009 is a controller that controls the ion beam generator 1002, the beam transport 1005, the rotating gantry 1006, and the irradiation system 1007 according to the treatment planning notified from the treatment planning system 1008 and irradiates the patient 2001 with the ion beam.

The control system 1009 includes a central control apparatus 1066, an accelerator and transport control apparatus 1069, a scanning control apparatus 1070, a rotation control apparatus 1071, and a database 1072.

According to the treatment planning notified from the treatment planning system 1008, the central control apparatus 1066 controls the ion beam generator 1002, the beam transport 1005, the rotating gantry 1006, and the irradiation system 1007 via the accelerator and transport control apparatus 1069, the scanning control apparatus 1070, and the rotation control apparatus 1071 to irradiate the patient 2001 with the ion beam.

The accelerator and transport control apparatus 1069 controls the ion beam generator 1002 and the beam transport 1005. The scanning control apparatus 1070 controls the irradiation system 1007. The scanning control apparatus 1070 controls the scanning magnet 1051 and the scanning magnet 1052 based on measurement results of the beam position monitor 1053 and the dose monitor 1054 to scan the ion beam. The rotation control apparatus 1071 controls the rotating gantry 1006. The database 1072 stores the treatment planning notified from the treatment planning system 1008. The database 1072 may store various types of information used in the central control apparatus 1066.

The central control apparatus 1066 includes a central processing unit (CPU) 1067, which is a central processing apparatus, and a memory 1068 connected to the CPU 1067. The database 1072, the accelerator and transport control apparatus 1069, the scanning control apparatus 1070, and the rotation control apparatus 1071 are electrically connected to the CPU 1067 in the central control apparatus 1066.

The CPU 1067 reads a computer program for controlling each device constituting the particle therapy system 1001 according to the treatment planning stored in the database 1072, and executes the read computer program to execute control processing for controlling each device in the particle therapy system 1001. The CPU 1067 controls each device by outputting a command to each device via the accelerator and transport control apparatus 1069, the scanning control apparatus 1070, and the rotation control apparatus 1071, and irradiates the patient 2001 with the ion beam according to the treatment planning. The memory 1068 is used as a work area of the computer program, and stores various types of data used and generated in the processing of the CPU 1067.

The computer program executed by the CPU 1067 may be one computer program or may be divided into a plurality of computer programs. Part or whole of the processing by the computer program may be achieved by dedicated hardware. The computer program may be installed in the central control apparatus 1066 from the database 1072, or may be installed in the central control apparatus 1066 from a program distribution server (not illustrated), an external storage medium, or the like. Each apparatus in the control system 1009 may be configured in a form in which two or more apparatuses are connected in a wired or wireless manner.

<Accelerator 1004>

Figure 2:
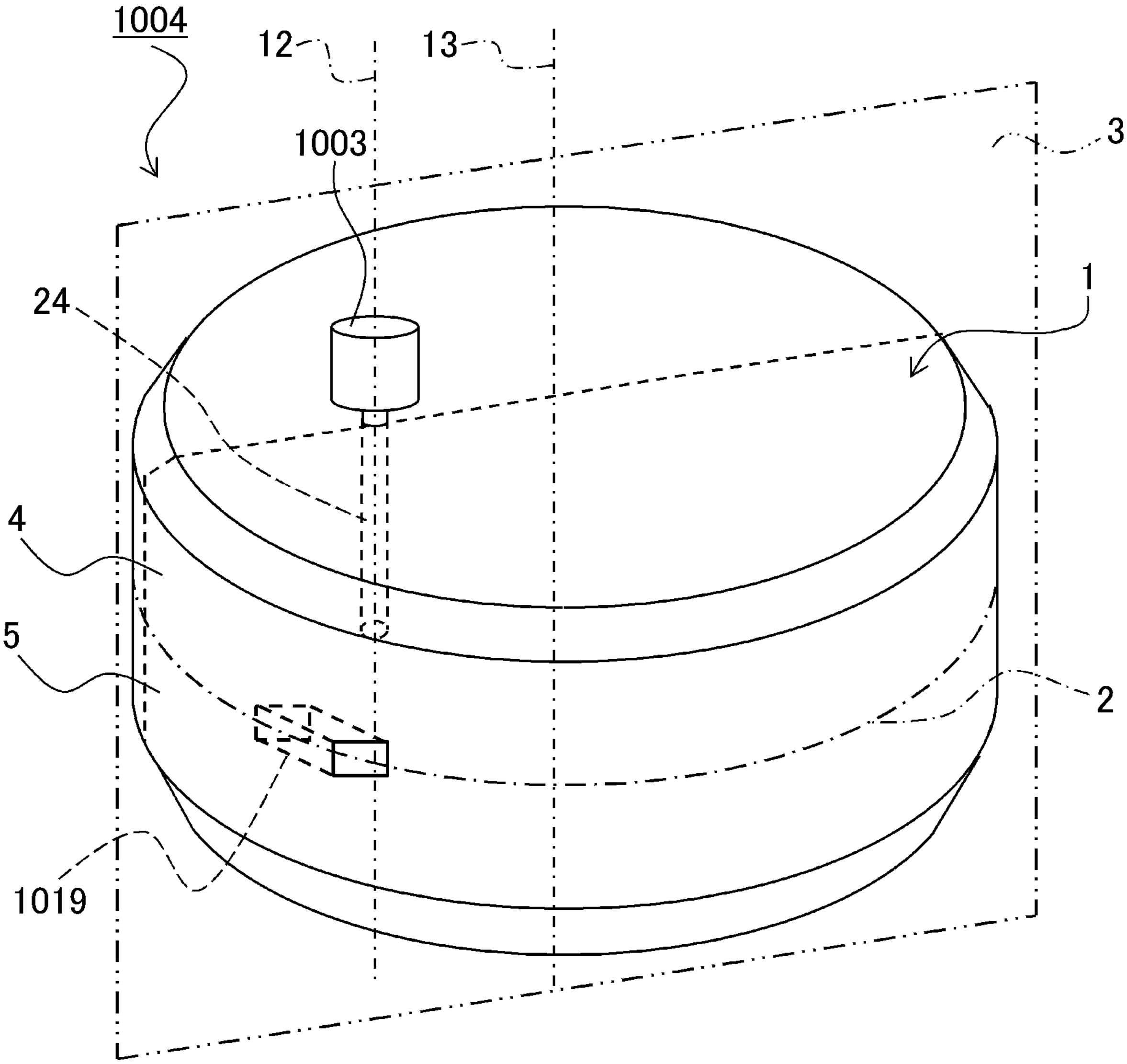
FIG. 2 is a perspective view of a main magnetic field magnet that generates a main magnetic field.
Figure 3:
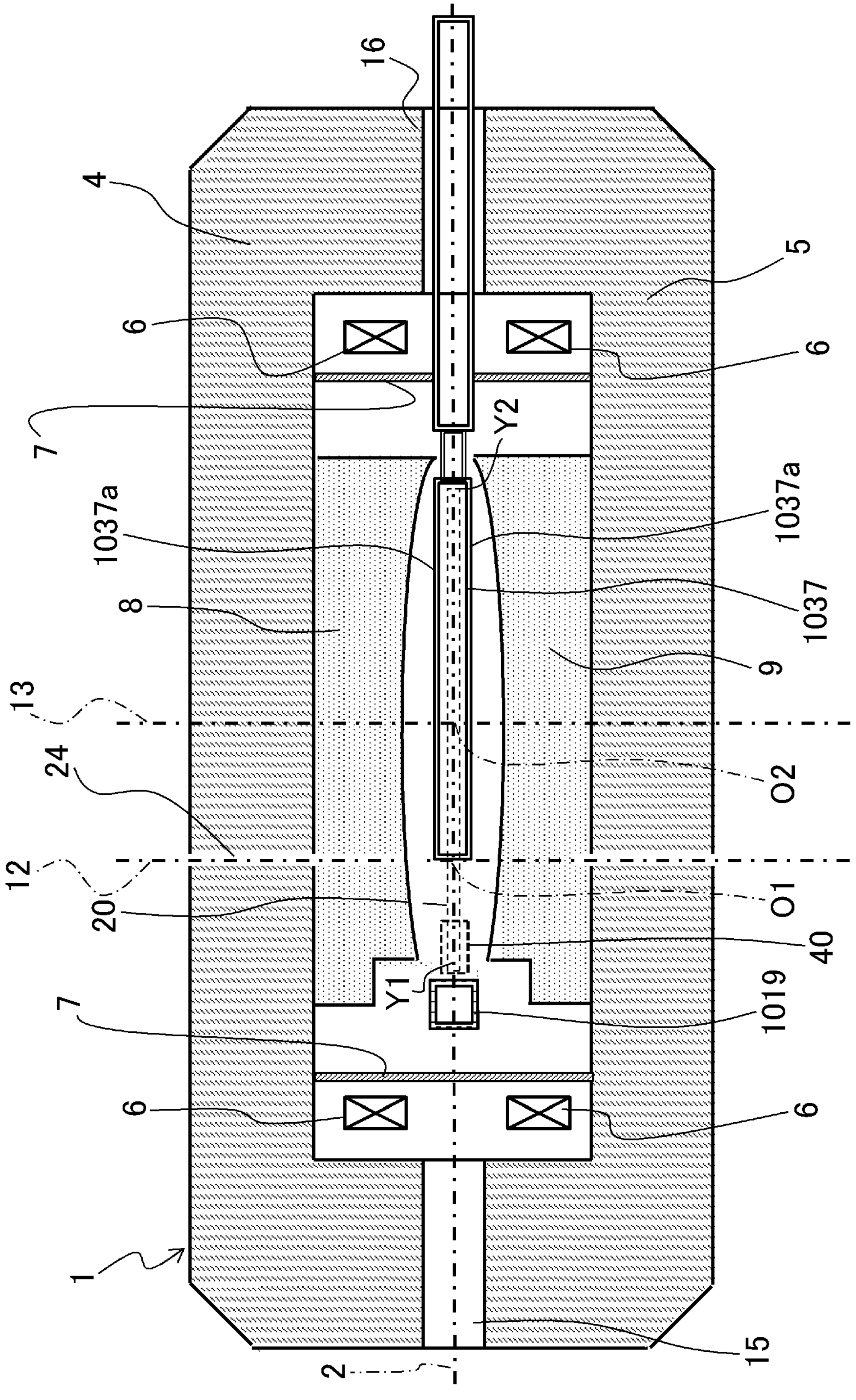
FIG. 3 is a longitudinal sectional view taken along a vertical plane of the main magnetic field magnet.
Figure 4:
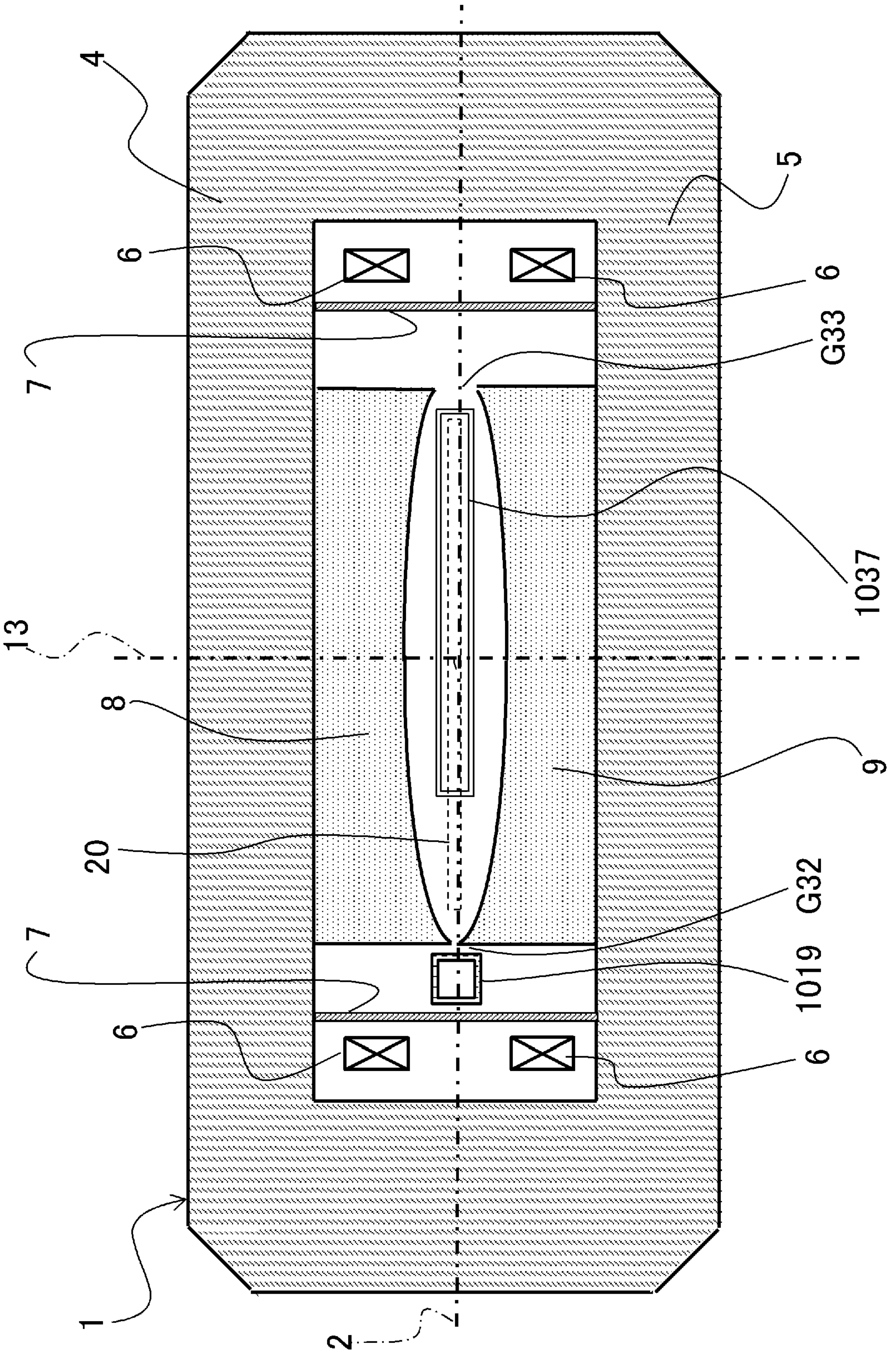
FIG. 4 is a longitudinal sectional view of the main magnetic field magnet including a regenerator.
Figure 5:
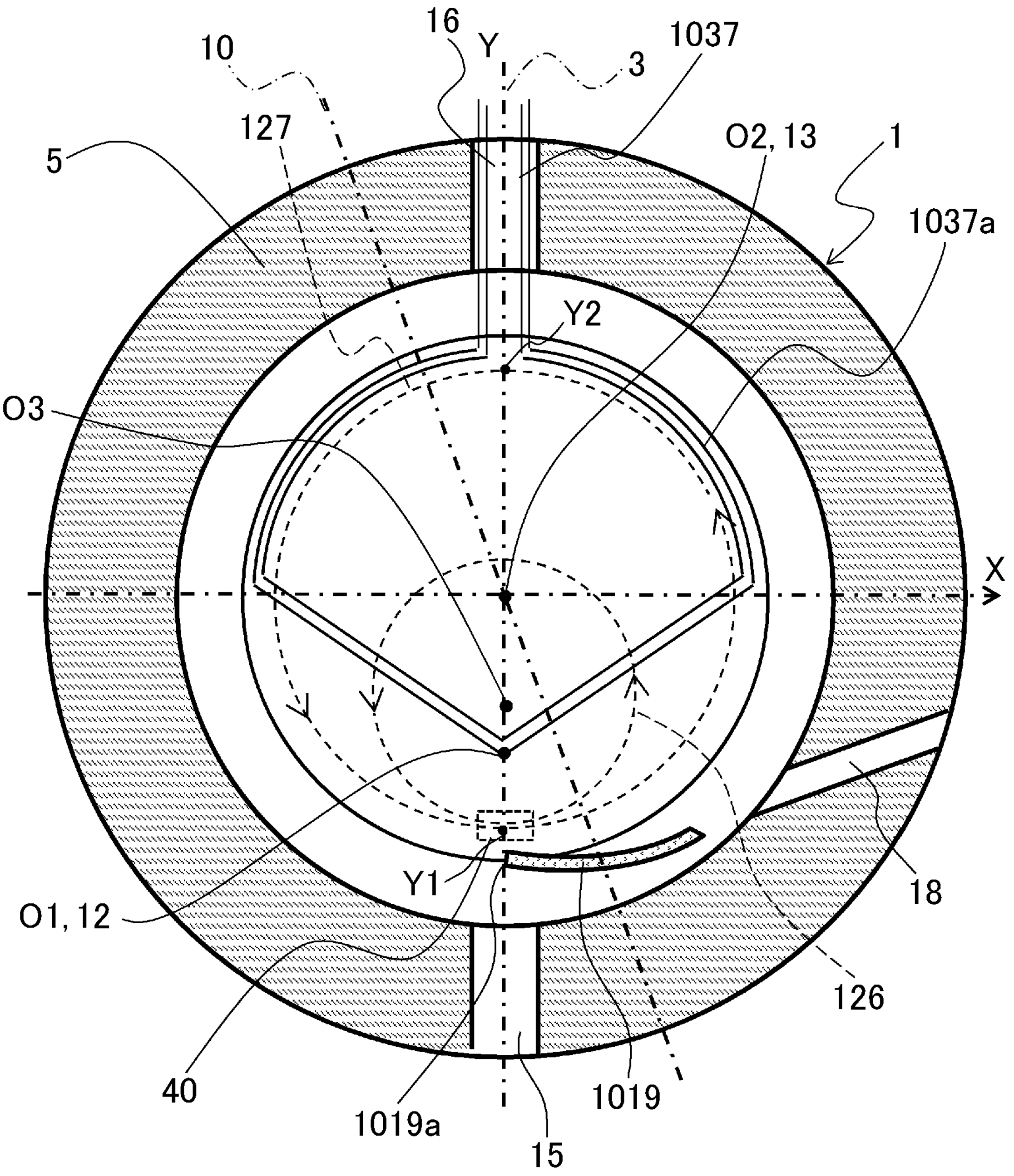
FIG. 5 is a transverse sectional view taken along a median plane of the main magnetic field magnet.

Next, the accelerator 1004 of the ion beam generator 1002 will be described in more detail with reference to FIGS. 1 to 4. FIG. 2 is a perspective view of the accelerator 1004. FIG. 3 is a longitudinal sectional view taken along a vertical plane 3 of the accelerator 1004. FIG. 4 is a longitudinal sectional view including a regenerator. FIG. 5 is a transverse sectional view taken along a median plane 2 of the accelerator 1004.

(Main Magnetic Field Magnet 1)

The accelerator 1004 has a main magnetic field magnet 1 as illustrated in FIGS. 2 to 5. The main magnetic field magnet 1 is a main magnetic field generation device that generates a main magnetic field for circulating an ion beam. As illustrated in FIG. 2, the main magnetic field magnet 1 has an upper return yoke 4 and a lower return yoke 5 which have a substantially disk shape when viewed from the vertical direction.

The upper return yoke 4 and the lower return yoke 5 have substantially vertically symmetrical shapes with respect to the median plane 2. The median plane 2 substantially passes through the center of the main magnetic field magnet 1 in the vertical direction and substantially coincides with an orbit plane drawn by the ion beam accelerated in the accelerator 1004.

The upper return yoke 4 and the lower return yoke 5 have shapes substantially plane-symmetrical with respect to the vertical plane 3 which is a plane substantially vertical to the median plane 2 and passing through the center of the main magnetic field magnet 1 in the median plane 2. In FIG. 2, a portion of the median plane 2 intersecting with the main magnetic field magnet 1 is indicated by an alternate long and short dash line, and a portion of the vertical plane 3 intersecting with the main magnetic field magnet 1 is indicated by a broken line.

In a space surrounded by the upper return yoke 4 and the lower return yoke 5, two coils 6 are arranged substantially plane-symmetrically with respect to the median plane 2 as illustrated in FIG. 3. The coil 6 is a superconducting coil, and is made of, for example, a superconducting wire material using a superconductor such as niobium titanium. The coils 6 are installed inside a cryostat (not illustrated), which is a cooling device for cooling the coils 6, and are cooled to be equal to or lower than a superconducting transition temperature by the cryostat. The coils 6 are drawn to the outside of the main magnetic field magnet 1 by a coil lead wire 1022 illustrated in FIG. 1 and connected to the coil excitation power supply 1057. The coil excitation power supply 1057 is a power supply that supplies power to the coils 6, and is controlled by the accelerator and transport control apparatus 1069.

A vacuum container 7 is provided on the inner side of the coils 6 in the space surrounded by the upper return yoke 4 and the lower return yoke 5. The vacuum container 7 is a container configured to keep the inside in a vacuum state, and is made of, for example, stainless steel. Inside the vacuum container 7, the upper magnetic pole 8 and the lower magnetic pole 9 are arranged plane-symmetrically with the median plane 2 interposed therebetween, and are coupled to the upper return yoke 4 and the lower return yoke 5, respectively. The upper return yoke 4, the lower return yoke 5, the upper magnetic pole 8, and the lower magnetic pole 9 are made of, for example, pure iron or low carbon steel having a reduced impurity concentration.

The main magnetic field magnet 1 having the above configuration forms a main magnetic field that feeds a magnetic field in an up-down direction to an internal acceleration space 20 having the median plane 2 at the center.

The intensity of the main magnetic field is designed such that ions supplied from the ion source 1003 stably circulate in the acceleration space 20 as the ion beam on the principle of weak focusing. The principle of weak focusing is a principle indicating that a main magnetic field monotonously decreases as approaching the outer periphery, and ions stably circulate as an ion beam when a gradient of the main magnetic field is included between a predetermined upper limit value and a lower limit value.

FIG. 4 is a longitudinal sectional view of the accelerator 1004 taken along a vertical plane passing through a regenerator region 32, and illustrates a gap spacing G32 at a position where the regenerator region 32 is interposed and a gap spacing G33 at a position where a substantially flat region 33 is interposed. As illustrated in FIG. 4, the gap spacing G33 is wider than the gap spacing G32.

In the present embodiment, a gap spacing between the upper magnetic pole 8 and the lower magnetic pole 9 at a position 41 where a peeler region 31 is interposed is significantly wider than the gap spacings at the position where the regenerator region 32 is interposed and the position where the substantially flat region 33 is interposed as illustrated in FIG. 3 in order to make a magnetic field gradient of the peeler region 31 greater than that of a comparative example.

Figure 6:
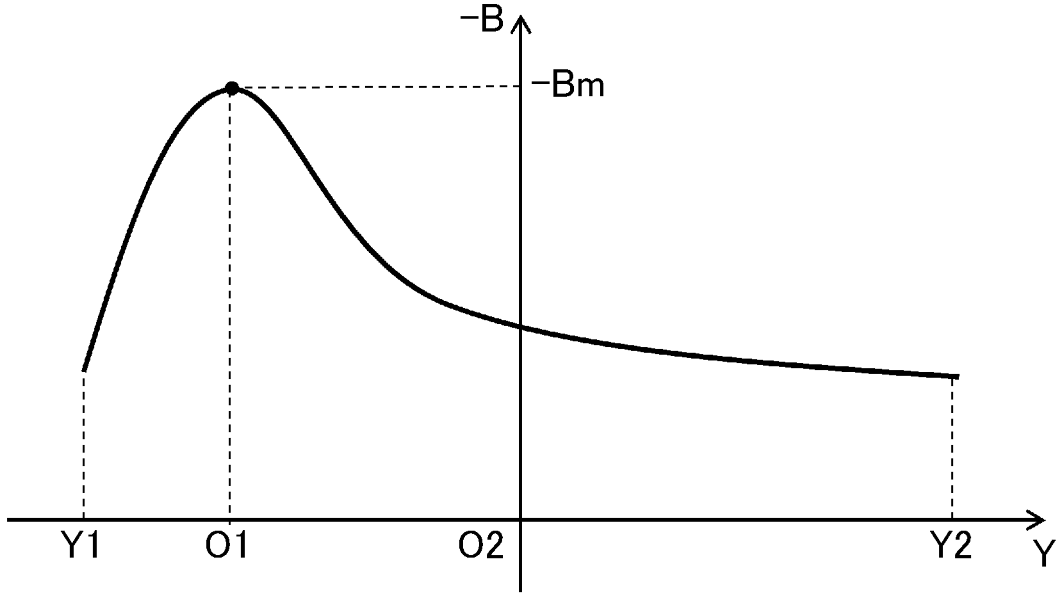
FIG. 6 is a view illustrating a magnetic field distribution on a center line of the main magnetic field.

FIG. 6 is a view illustrating an intensity distribution on a center line of the main magnetic field. The center line is an intersection line between the median plane 2 and the vertical plane 3. In the present embodiment, a direction along the intersection line is a Y-axis direction, and a direction vertical to the Y-axis direction on the median plane 2 is an X-axis direction.

As illustrated in FIG. 6, the intensity of the main magnetic field is the highest at a predetermined position O1 shifted in the Y-axis direction from a magnetic pole center O2, which is the center of the upper magnetic pole 8 and the lower magnetic pole 9 in a direction of the median plane 2, and gradually decreases as approaching the outer peripheries of the upper magnetic pole 8 and the lower magnetic pole 9. Hereinafter, the position O1 is sometimes referred to as the center of a main magnetic field distribution.

(Ion Source 1003)

In the example of FIG. 2, the ion source 1003 is installed on the main magnetic field magnet 1. The upper return yoke 4 and the upper magnetic pole 8 are provided with a through hole 24 configured to guide ions from the ion source 1003 to the position O1 of the acceleration space 20. A central axis (ion entrance axis) 12 of the through hole 24 is substantially vertical to the median plane 2 and passes even through the position O1. The ion source 1003 is arranged in an upper portion of the through hole 24, and introduces the ions into the position O1 of the acceleration space 20 through the through hole 24.

The ion source 1003 may be installed inside the main magnetic field magnet 1. In this case, the through hole 24 is unnecessary.

(Magnetic Channel 1019)

As illustrated in FIGS. 2 to 5, the accelerator 1004 has the magnetic channel 1019 that extracts an ion beam and transports the ion beam to the beam transport 1005. The magnetic channel 1019 is arranged on the outer side of the acceleration space 20, for example, in an outer peripheral portion closer to the center O1 of the main magnetic field distribution on the Y axis of the upper magnetic pole 8 and the lower magnetic pole 9. The magnetic channel 1019 has an opening 1019*a* in the vicinity of the Y axis, takes in an ion beam of a desired energy from the opening 1019*a*, and transports the ion beam to the outside of the accelerator 1004 through a through hole 18 provided in the upper return yoke 4 and the lower return yoke 5. A distal end of the beam transport 1005 is installed in the through hole 18, and the extracted ion beam is guided to the irradiation system 1007 via the beam transport 1005.

(Radiofrequency Acceleration Cavity 1037)

The accelerator 1004 has the radiofrequency acceleration cavity 1037. The radiofrequency acceleration cavity 1037 is a member configured to accelerate ions entering the acceleration space 20 to form an ion beam. The radiofrequency acceleration cavity 1037 includes a pair of dee electrodes 1037*a* arranged with the median plane 2 interposed therebetween. The dee electrode 1037*a* has a fan shape when viewed from the vertical direction. The dee electrode 1037*a* is arranged to have an apex (center) of the fan shape in the vicinity of the center O1 of the main magnetic field distribution and to cover a part of an orbit of the ion beam including the magnetic pole center O2.

A ground electrode (not illustrated) is arranged so as to face a radial end surface of the dee electrode 1037*a*, and an acceleration electric field, which is an accelerating radiofrequency electric field for accelerating the ion beam, is formed between the radial end surface of the dee electrode 1037*a* and the ground electrode.

Since the dee electrode 1037*a* is formed in the fan shape having the position O1 as the apex, it is possible to feed the acceleration electric field such that a traveling direction of the circulating ion beam is parallel to the acceleration electric field, that is, to a position where an axis, which passes through the center of each closed orbit in which the ion beam circulates and is parallel to the X axis, intersects with each closed orbit.

The radiofrequency acceleration cavity 1037 is led out to the outside of the main magnetic field magnet 1 through a through hole 16 provided between the upper return yoke 4 and the lower return yoke 5 along the Y-axis direction, and is connected to a waveguide 1010 outside the main magnetic field magnet 1. The radiofrequency power supply 1036 is connected to the waveguide 1010. The radiofrequency power supply 1036 is a power supply that supplies power to the radiofrequency acceleration cavity 1037 through the waveguide 1010, and is controlled by the accelerator and transport control apparatus 1069. The power supplied from the radiofrequency power supply 1036 excites the radiofrequency electric field as the acceleration electric field between the dee electrode 1037*a* and the ground electrode.

An orbit radius of the closed orbit, which is an orbit of the ion beam that circulates in the acceleration space 20, gradually increases with the acceleration of the ion beam as will be described later. The acceleration electric field needs to be synchronized with the ion beam in order to appropriately accelerate the ion beam. For this purpose, it is necessary to modulate a resonance frequency of the radiofrequency acceleration cavity 1037 according to the energy of the ion beam. The resonance frequency is modulated, for example, by adjusting inductance or electrostatic capacitance of the radiofrequency acceleration cavity 1037. As an adjustment method for adjusting the inductance or electrostatic capacitance of the radiofrequency acceleration cavity 1037, a known method can be used. For example, in the case of adjusting the electrostatic capacitance, the resonance frequency is modulated by controlling capacitance of a variable capacitance capacitor connected to the radiofrequency acceleration cavity 1037.

(Sparseness and Denseness of Closed Orbits)

Figure 7:
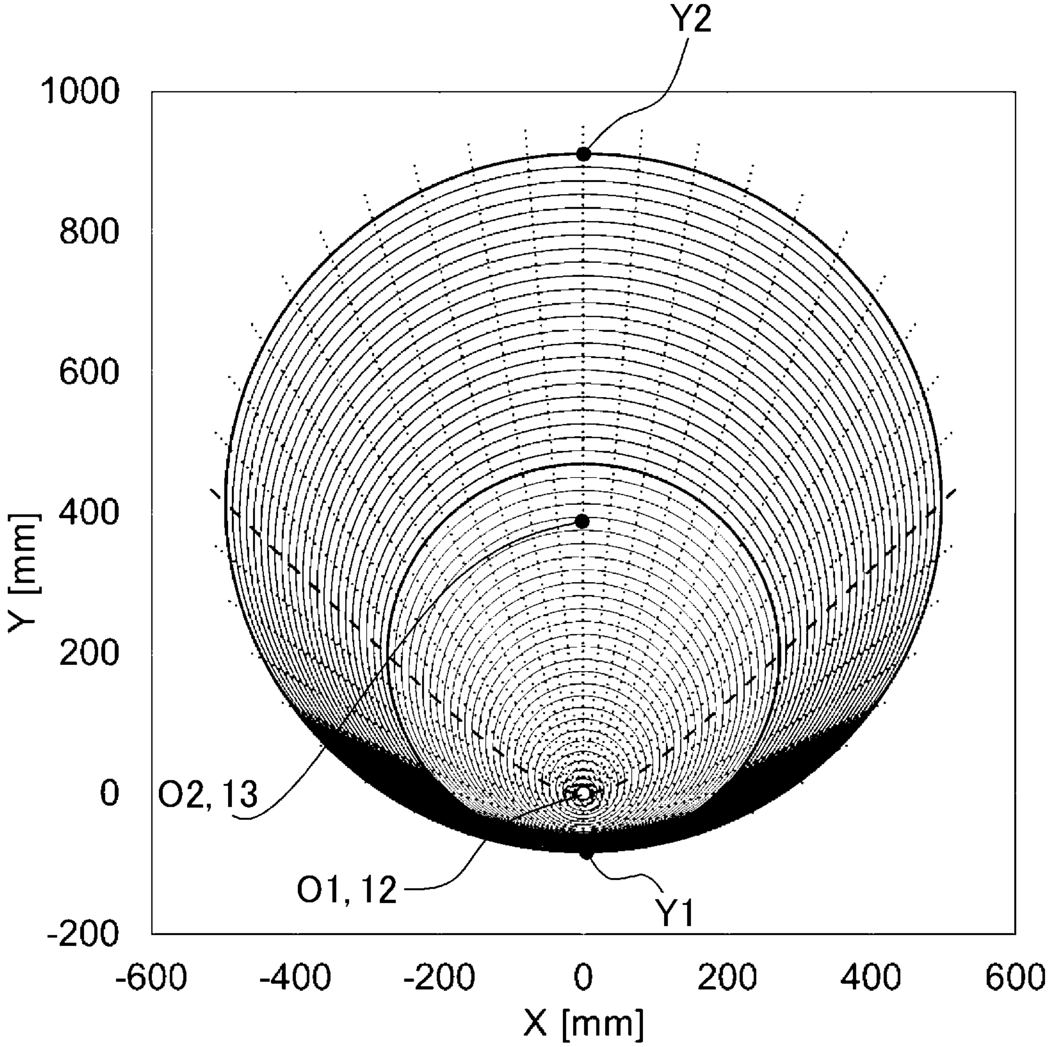
FIG. 7 is a view for describing closed orbits of an ion beam.

FIG. 7 is a view for describing a closed orbit of an ion beam that circulates in the acceleration space 20, and illustrates closed orbits 126 of ion beams having different energies.

Ions introduced from the ion source 1003 into the acceleration space 20 are formed as ion beams by the radiofrequency electric field, which is the acceleration electric field, and circulate in the acceleration space 20. As illustrated in FIG. 6, the main magnetic field in the acceleration space 20 is maximum at the position O1 shifted from the magnetic pole center O2, and gradually decreases as approaching the outer peripheries of the upper magnetic pole 8 and the lower magnetic pole 9. In this case, an ion beam with a lower energy circulates along an orbit having the position O1 at the center. As the ion beam is accelerated by the radiofrequency electric field, the orbit radius increases, and the center of the orbit gradually approaches the position O2 of a central axis 13 of the upper magnetic pole 8 and the lower magnetic pole 9. The closed orbit 127 of an ion beam having the maximum energy illustrated in FIG. 5 has a shape substantially along the outer peripheries of the upper magnetic pole 8 and the lower magnetic pole 9, and the center thereof substantially coincides with the position O2.

Therefore, the closed orbits 126 of the ion beams are dense between the position O1 and a position Y1 of an end portion of the acceleration space 20 in the Y-axis direction, and are sparse between the position O1 and a position Y2 of an end portion in the Y-axis direction on the opposite side across the position O2 of the centers of the upper magnetic pole 8 and the lower magnetic pole 9 as illustrated in FIG. 7.

For example, as illustrated in FIG. 5, the center of the closed orbit 126 of the maximum energy beam corresponding to the maximum energy (235 Mev) of the ion beams that can be extracted among the closed orbits 127 substantially coincides with the magnetic pole center O2. A center O3 of the closed orbit 126 of the lowest energy beam corresponding to the lowest energy of the ion beams that can be extracted is on a line segment connecting the magnetic pole center O2 and the center O1 of the main magnetic field distribution.

(Extraction of Ion Beam)

Figure 8:
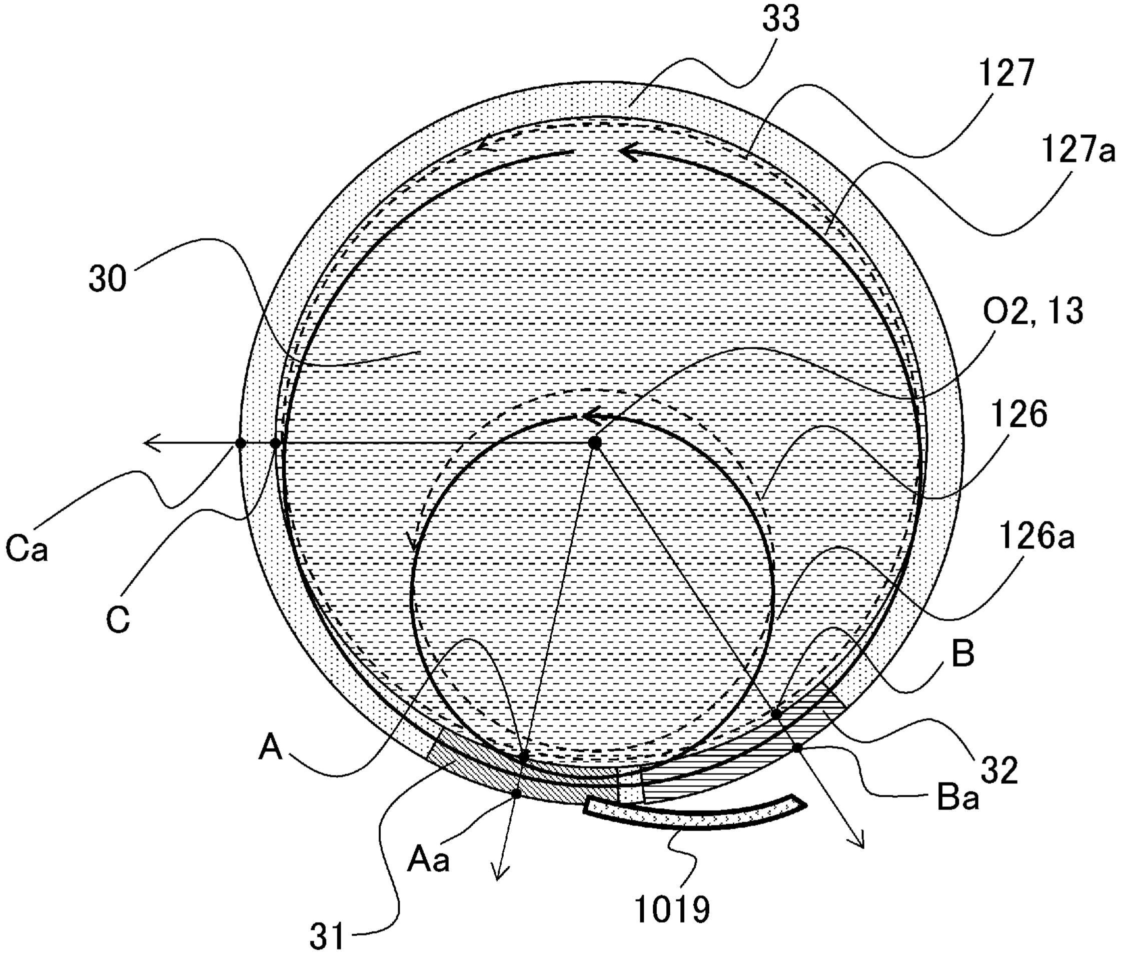
FIG. 8 is a schematic view schematically illustrating a magnetic field distribution on the median plane of the main magnetic field.

As illustrated in FIG. 8, the accelerator 1004 includes a radiofrequency kicker 40, the peeler region 31, the regenerator region 32, and the substantially flat region 33 as a mechanism for guiding ion beams circulating in the acceleration space 20 to the magnetic channel 1019, and extracts an ion beam having an energy in a predetermined range using the density of the closed orbit 126.

The radiofrequency kicker 40 is a displacement unit that displaces the ion beam circulating in the main magnetic field region where the main magnetic field is excited in the acceleration space 20 to the outer side. The radiofrequency kicker 40 feeds, for example, a horizontal radiofrequency electric field to the ion beam to increase the amplitude of the betatron oscillation of the ion beam. Accordingly, the ion beam is displaced so as to pass through the peeler region 31, the regenerator region 32, and the substantially flat region 33. The peeler region 31, the regenerator region 32, and the substantially flat region 33 constitute a disturbance magnetic field region that disturbs the ion beam displaced by the radiofrequency kicker 40 to excite the magnetic field guided to the magnetic channel 1019.

FIG. 8 is a view for describing the arrangement of the peeler region 31, the regenerator region 32, and the substantially flat region 33, and illustrates a magnetic field distribution on the median plane 2 where the ion beam circulates.

The magnetic field distribution illustrated in FIG. 6 is formed in a main magnetic field region 30 illustrated in FIG. 8. The peeler region 31, the regenerator region 32, and the substantially flat region 33 are formed at a magnetic pole peripheral edge portion on the outer side of the main magnetic field region 30. The peeler region 31 and the regenerator region 32 are located on the outer side of a dense region where the closed orbits 126 of the ion beams in the main magnetic field region 30 are dense.

Figure 9:
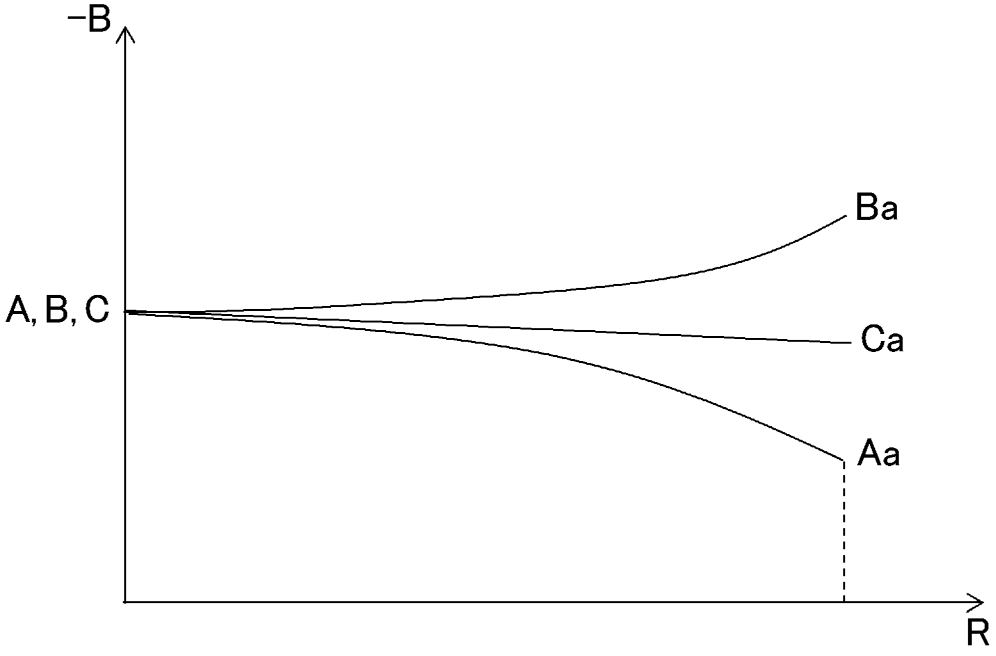
FIG. 9 is a view illustrating a radial distribution of a magnetic field on a median plane at a magnetic pole peripheral edge portion.

FIG. 9 is a view illustrating radial distributions of magnetic fields in the peeler region 31, the regenerator region 32, and the substantially flat region 33. The magnetic field distribution in the peeler region 31 corresponds to a magnetic field distribution along line A-Aa in FIG. 8. The magnetic field distribution of the regenerator region 32 corresponds to a magnetic field distribution along line B-Ba in FIG. 8. The magnetic field distribution in the substantially flat region 33 corresponds to a magnetic field distribution along line C-Ca in FIG. 8.

The magnetic fields at the innermost positions (Positions A, B, C) of the peeler region 31, the regenerator region 32, and the substantially flat region 33 substantially coincide with each other. The peeler region 31 is a first region in which the intensity of the magnetic field decreases relatively greatly as approaching the outer side (from A toward Aa). The regenerator region 32 is a second region in which the intensity of the magnetic field increases relatively greatly as approaching the outer side (from B toward Ba). The substantially flat region 33 is a third region in which the magnetic field is substantially constant. In the present embodiment, the magnetic field of the substantially flat region 33 gradually and slightly decreases from the magnetic field of the peeler region 31 as proceeding toward the outer side (from C to Ca). Therefore, in outer peripheral portions of the respective regions, the magnetic field of the peeler region 31 is the lowest, the magnetic field of the regenerator region 32 is the highest, and the magnetic field of the substantially flat region 33 has a magnitude between the magnetic fields of the peeler region 31 and the regenerator region 32.

Hereinafter, an operation at the time of extracting an ion beam having a desired energy from the accelerator 1004 will be described.

The accelerator and transport control apparatus 1069 causes the ion source 1003 to generate ions according to a command from the central control apparatus 1066, and introduces the ions to the position O1 in the acceleration space 20 in the main magnetic field magnet 1 through the through hole 24. The accelerator and transport control apparatus 1069 generates the acceleration electric field in the acceleration space 20 using the radiofrequency acceleration cavity 1037, and accelerates the ions to form the ion beam. The formed ion beam increases the energy while circulating.

When the ion beam reaches the desired energy, the accelerator and transport control apparatus 1069 turns off the power supplied to the radiofrequency acceleration cavity 1037 and turns on the radiofrequency kicker 40. Accordingly, the radiofrequency electric field is fed to the ion beam in superposition with the main magnetic field. As a result, the closed orbit 126 of the ion beam is displaced in the radial direction (direction approaching the position Y1). For example, as illustrated in FIG. 8, when the ion beam is the lowest energy beam, the closed orbit 126 is displaced in the radial direction like a closed orbit 126*a*. When the ion beam is the maximum energy beam, the closed orbit 127 is displaced in the radial direction like a closed orbit 127*a*.

As a result, the ion beam passes through the peeler region 31 and the regenerator region 32. Accordingly, resonance of horizontal betatron oscillation called "2/2 resonance" is generated, and the ion beam diverges in the radial direction and reaches the opening 1019*a* of the magnetic channel 1019. The ion beam is completely separated from the closed orbit by the magnetic channel 1019 and transported to the outside of the accelerator 1004 through the through hole 18.

In the present embodiment, the energy of the ion beam to be extracted is variable. Therefore, it is necessary to form the peeler region 31 and the regenerator region 32 in a region where not only the maximum energy beam but also the minimum energy beam passes.

Details of the magnetic channel 1019 of the present embodiment will be described with reference to FIGS. 10 to 16. The magnetic channel 1019 of the present embodiment includes a predetermined mechanism 50 that suppresses a magnetic field gradient generated radially inward in the circulating ion beam region 54. The predetermined mechanism 50 can also be referred to as the mechanism 50 that suppresses the magnetic gradient.

Figure 10:
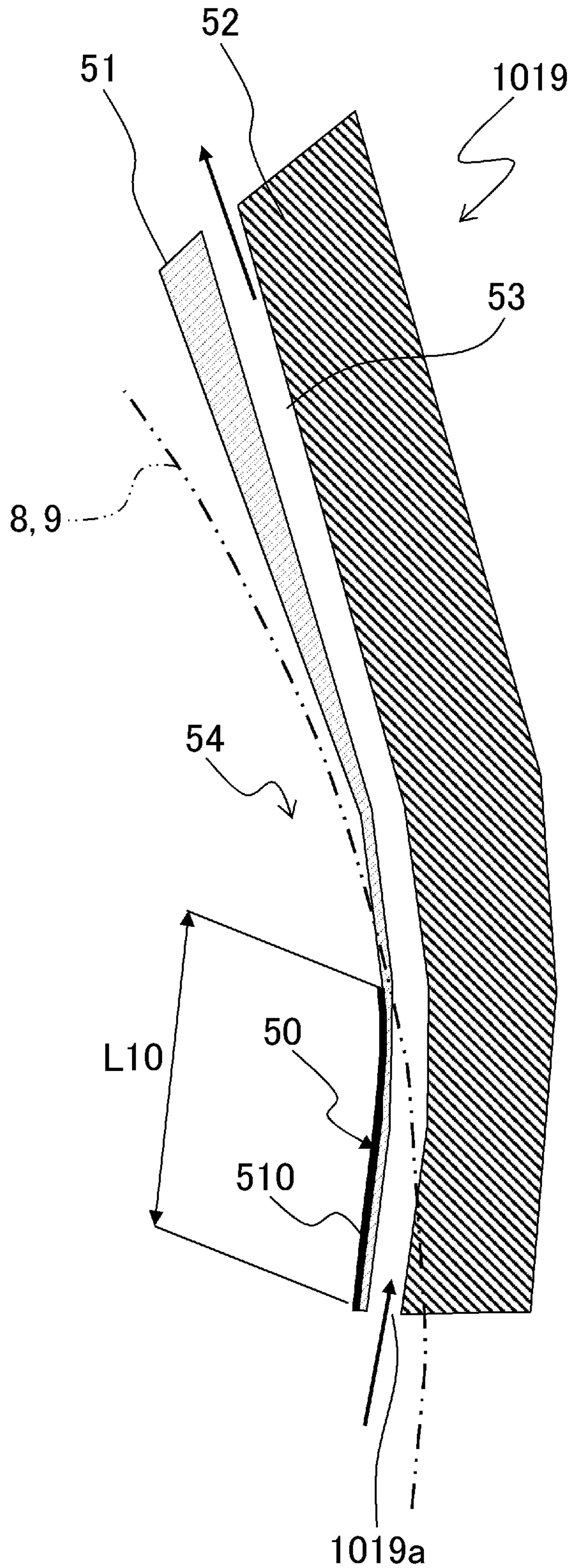
FIG. 10 is a plan view illustrating a magnetic channel in a state where an upper return yoke and an upper magnetic pole are removed.

FIG. 10 is a plan view illustrating the magnetic channel 1019 in a state where the upper return yoke 4 and the upper magnetic pole 8 are removed.

As described above, the magnetic channel 1019 is a member configured to transport the ion beam to the outside of the accelerator 1004, and is provided in the main magnetic field magnet 1. The magnetic channel 1019 is a magnetic structure including a septum 51 located on the radially inner side and an anti-septum 52 located on the radially outer side. A beam extraction passage 53 is formed between the septum 51 and the anti-septum 52. The septum 51 is an example of a "first member". The anti-septum 52 is an example of a "second member".

A radial width dimension of the septum 51 is set to be smaller than a radial width dimension of the anti-septum 52. The radial width dimension is a width dimension along the substantially radial direction of the main magnetic field magnet 1, and is a dimension along the left-right direction in FIG. 10. The width dimension of the septum 51 is smaller than the width dimension of the anti-septum 52 over the entire length.

As illustrated in FIGS. 11 to 14, the predetermined mechanism 50 is achieved, for example, by setting a radial width dimension W3 of a predetermined region where the median plane 2, orthogonal to an axial middle of the main magnetic field magnet 1, intersects with the septum 51 to the minimum.

For example, the predetermined mechanism 50 is achieved by forming a recessed part 510 in the predetermined region where the median plane 2 intersects with the septum 51.

For example, the predetermined mechanism 50 is achieved by setting a radial width dimension W1 of the septum 51 to be smaller than the radial width dimension of the anti-septum 52, and forming the recessed part 510 in the predetermined region where the median plane 2, orthogonal to the axial middle of the main magnetic field magnet 1, intersects with the septum 51 to set the radial width dimension W3 of the septum 51 to the minimum.

The recessed part 510 is formed over a predetermined length range L10 from a position corresponding to an inlet side 1019*a* of the beam extraction passage 53. A standard of the predetermined length range L10 is a length by which the septum 51 is interposed between the upper magnetic pole 8 and the lower magnetic pole 9. A radial width of the septum 51 is thin at a position interposed between the upper magnetic pole 8 and the lower magnetic pole 9, and increases as the septum 51 extends radially outward from an outer periphery of the magnetic pole and the distance between the septum 51 and the outer periphery of the magnetic pole becomes large.

A traverse section of the recessed part 510 may be formed so as to spread from a bottom center of the recessed part 510 toward an opening side.

Figure 11:
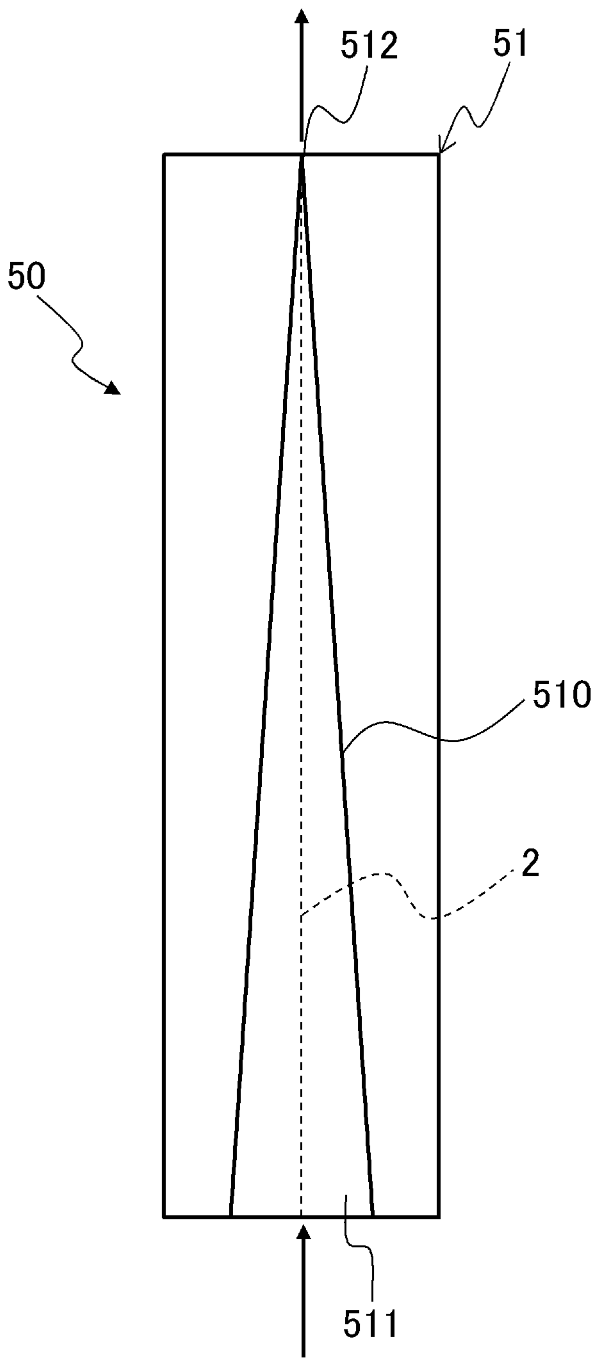
FIG. 11 is a plan view illustrating an example of the inner side of a septum.

FIG. 11 is a plan view of the septum 51 as viewed from the radially inner side. The recessed part 510 can be formed in the septum 51 such that a width of the recessed part 510 gradually decreases from a start end 511 toward a terminal end 512 in the circumferential direction of the beam.

Figure 13:
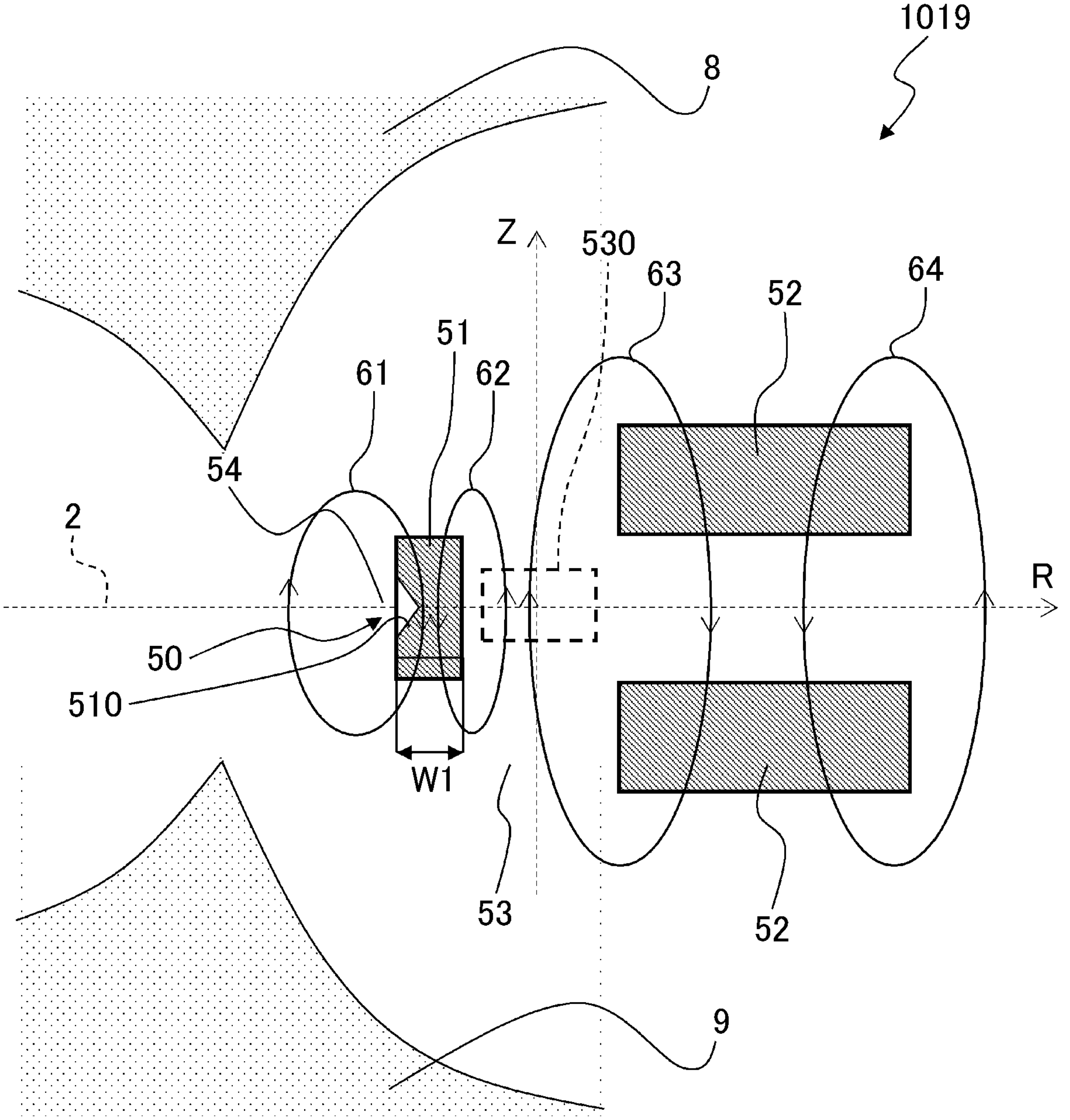
FIG. 13 is an explanatory view schematically illustrating a cross section of the magnetic channel according to the present disclosure.
Figure 14:
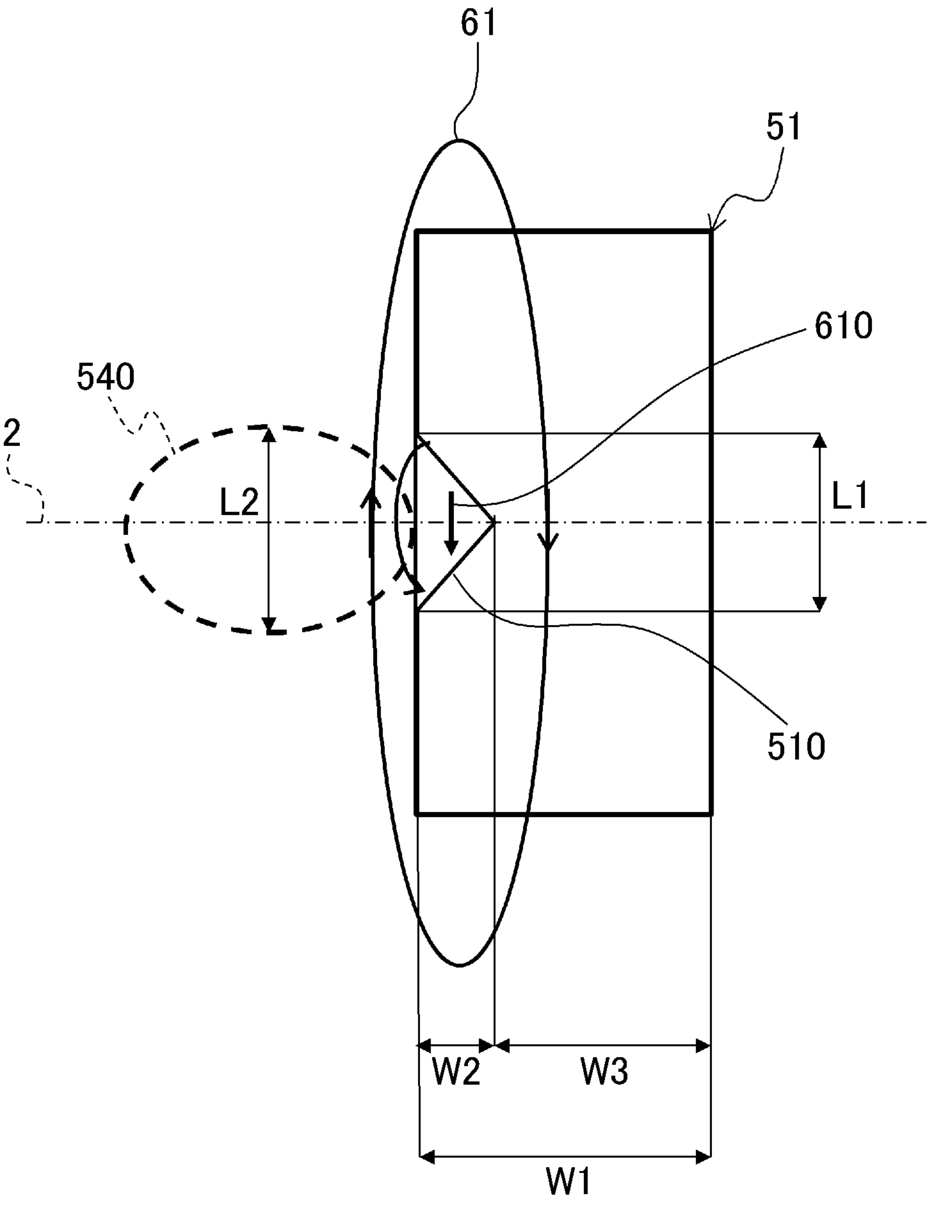
FIG. 14 is an explanatory view schematically illustrating a relationship between a recessed part formed on the inner side of the septum, an ion beam, and a magnetic field.

As illustrated in FIGS. 13 and 14, a shape of the traverse section of the recessed part 510 can be formed in a triangular shape, a wedge shape, an elliptical shape, or a circular shape expanding toward the opening side. Accordingly, it is possible to suppress the decrease in the magnetic field on the radially outer side of the septum 51 as will be described later with reference to FIG. 15.

Figure 12:
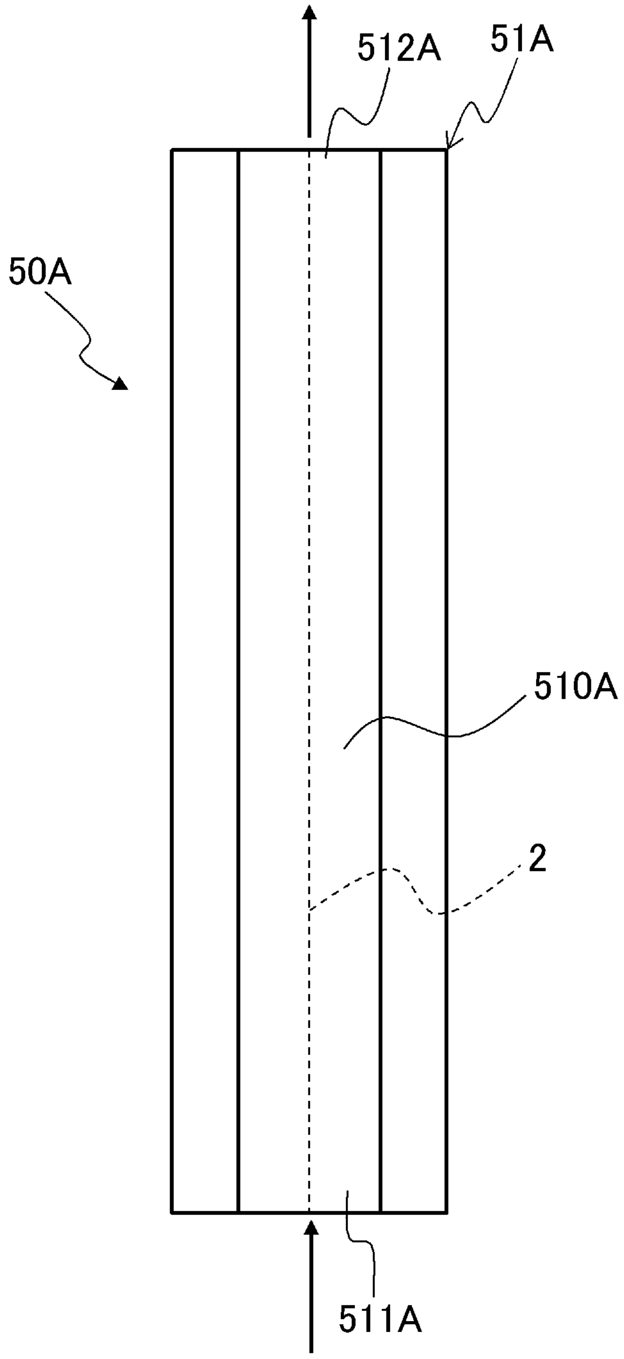
FIG. 12 is a plan view illustrating another example of the inner side of the septum.

FIG. 12 is a plan view of a septum 51A of another example as viewed from the radially inner side. The septum 51A of this modification has a recessed part 510A having a rectangular cross section, and a width dimension is constant from a starting end 511A to a terminal end 512A of the recessed part 510A.

FIG. 13 is an explanatory view schematically illustrating a cross section of the magnetic channel 1019. The circulating beam region 54 is located on the radially inner side of the septum 51, and a region 530 of the beam to be extracted is located in the beam extraction passage 53 between the radially outer side of the septum 51 and the radially inner side of the anti-septum 52.

FIG. 14 schematically illustrates a relationship among the recessed part 510 formed on the inner side of the septum 51, an ion beam, and a magnetic field.

The septum 51 has a width dimension W1 in a direction along the radial direction of the main magnetic field magnet 1. However, when attention is paid to a position where the recessed part 510 is formed, the width dimension W1 is reduced by a depth dimension W2 of the recessed part 510 to be a dimension W3 (W3=W1−W2).

Assuming that an approximate size of a region in which the beam circulates is a circulating beam 540, a height dimension (dimension in a direction along an axial direction of the main magnetic field magnet 1) L2 of the circulating beam 540 is substantially equal to or larger than a dimension L1 on the opening side of the recessed part 510 (L2≥L1). In other words, the opening width L1 of the recessed part 510 is set to be equal to or smaller than the height dimension L2 of the circulating beam 540.

Accordingly, the circulating beam 540 is close to the inner side of the septum 51 and is affected by a leakage magnetic flux 610 flowing in the recessed part 510. Since a direction of the leakage magnetic flux 610 appearing in the recessed part 510 is opposite to that of a magnetic flux 61 passing through the septum 51 and returning to the outside, a magnetic field gradient in the vicinity of the recessed part 510 is suppressed. Therefore, the influence of the magnetic field gradient in the vicinity of the inner side of the septum 51 on the circulating beam 540 can be suppressed, and the beam to be transferred to the extraction region 530 can be efficiently extracted.

Figure 15:
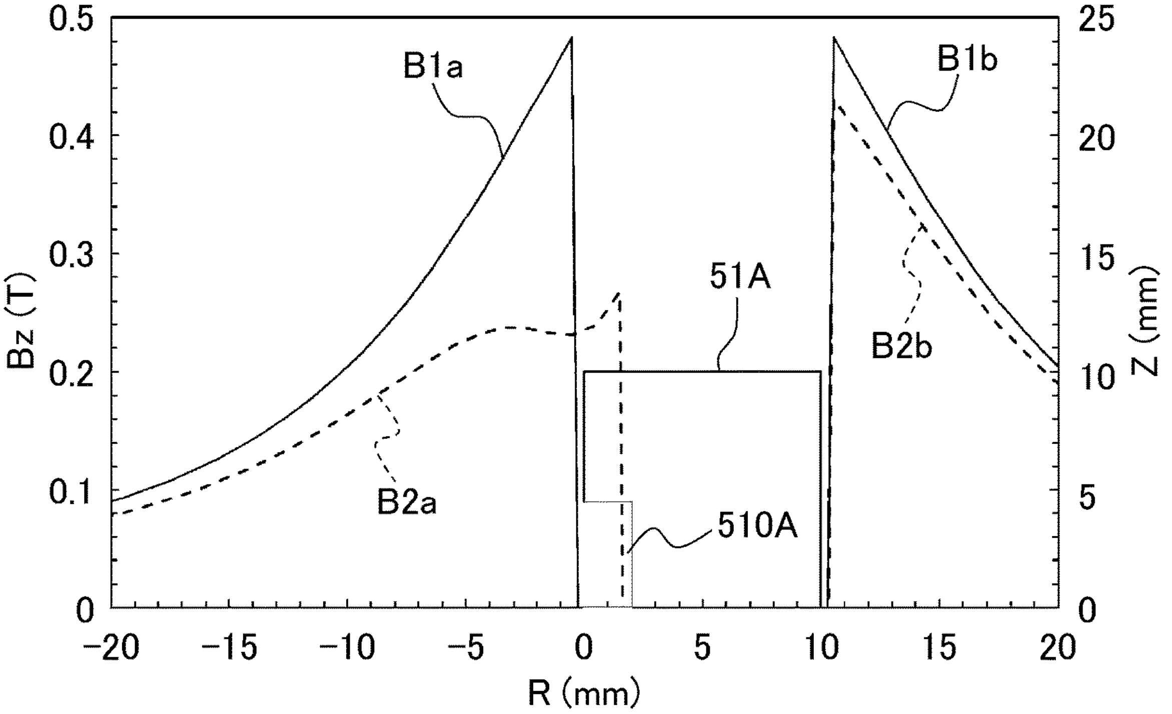
FIG. 15 is an explanatory view illustrating a magnetic field in the vicinity of the septum.

FIG. 15 is an explanatory view illustrating a magnetic field in the vicinity of the septum 51. Here, the description will be given using the septum 51A, which has the recessed part 510A having the rectangular cross section, as an example. The vertical axis on the left side in FIG. 15 represents the intensity (T) of the magnetic field. The vertical axis on the right side in FIG. 15 represents a height dimension (mm) along the axial direction of the main magnetic field magnet 1, and the horizontal axis on the lower side in FIG. 15 represents a dimension (mm) along the radial direction of the main magnetic field magnet 1.

A magnetic field B2*a* generated in the recessed part 510A is lower than a magnetic field B1*a* generated in the septum 51 that does not have the recessed part 510A. This is because a magnetic field in a direction opposite to the magnetic field B1*a* is generated in the recessed part 510A to suppress the magnetic field B1*a*.

When attention is paid to a magnetic field on the radially outer side of the septum 51A, a magnetic field B2*b* on the radially outer side of the septum 51A having the recessed part 510A is slightly decreased as compared with a magnetic field B1*b* on the radially outer side of the septum 51 that does not have the recessed part 510A.

Figure 16:
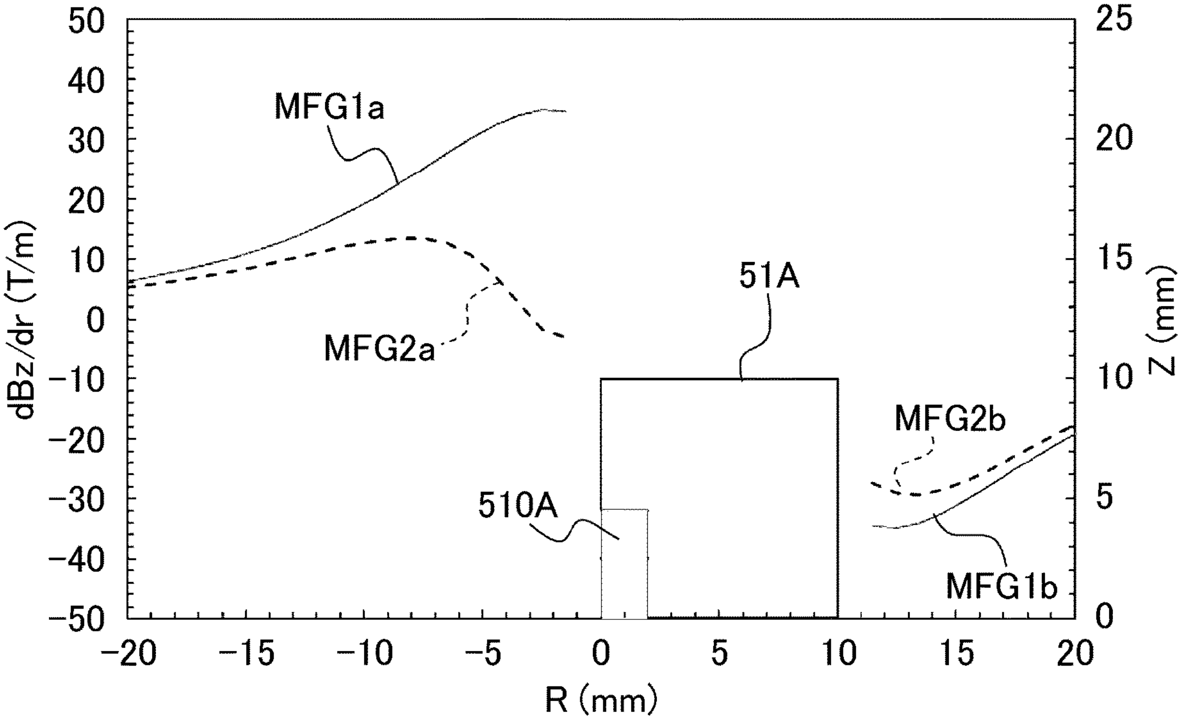
FIG. 16 is an explanatory view illustrating a magnetic field gradient in the vicinity of the septum.

FIG. 16 illustrates a magnetic field gradient in the vicinity of the septum. The vertical axis on the left side in FIG. 16 represents a magnetic field gradient (T/m), the vertical axis on the right side in FIG. 16 represents a height dimension (mm) along the axial direction of the main magnetic field magnet 1, and the horizontal axis on the lower side in FIG. 16 represents a dimension (mm) along the radial direction of the main magnetic field magnet 1.

A magnetic field gradient MFG2*a* of the septum 51A having the recessed part 510A is gentler than a magnetic field gradient MFG1*a* in the case of the septum 51 that does not have the recessed part 510A. When attention is paid to a magnetic field gradient on the radially outer side of the septum 51, a magnetic field gradient MFG2*b* in the case where the recessed part 510A is provided changes more gently than a magnetic field gradient MFG1*b* of the septum 51 that does not have the recessed part 510A.

According to the present embodiment configured in this manner, the magnetic channel 1019 includes the predetermined mechanism 50 that suppresses the magnetic field gradient generated on the radially inner side in the circulating beam region. Thus, it is possible to suppress the influence of the rapidly changing magnetic field gradient from acting on the circulating beam, and it is possible to prevent the attenuation of the beam and efficiently extract the beam.

Figure 17:
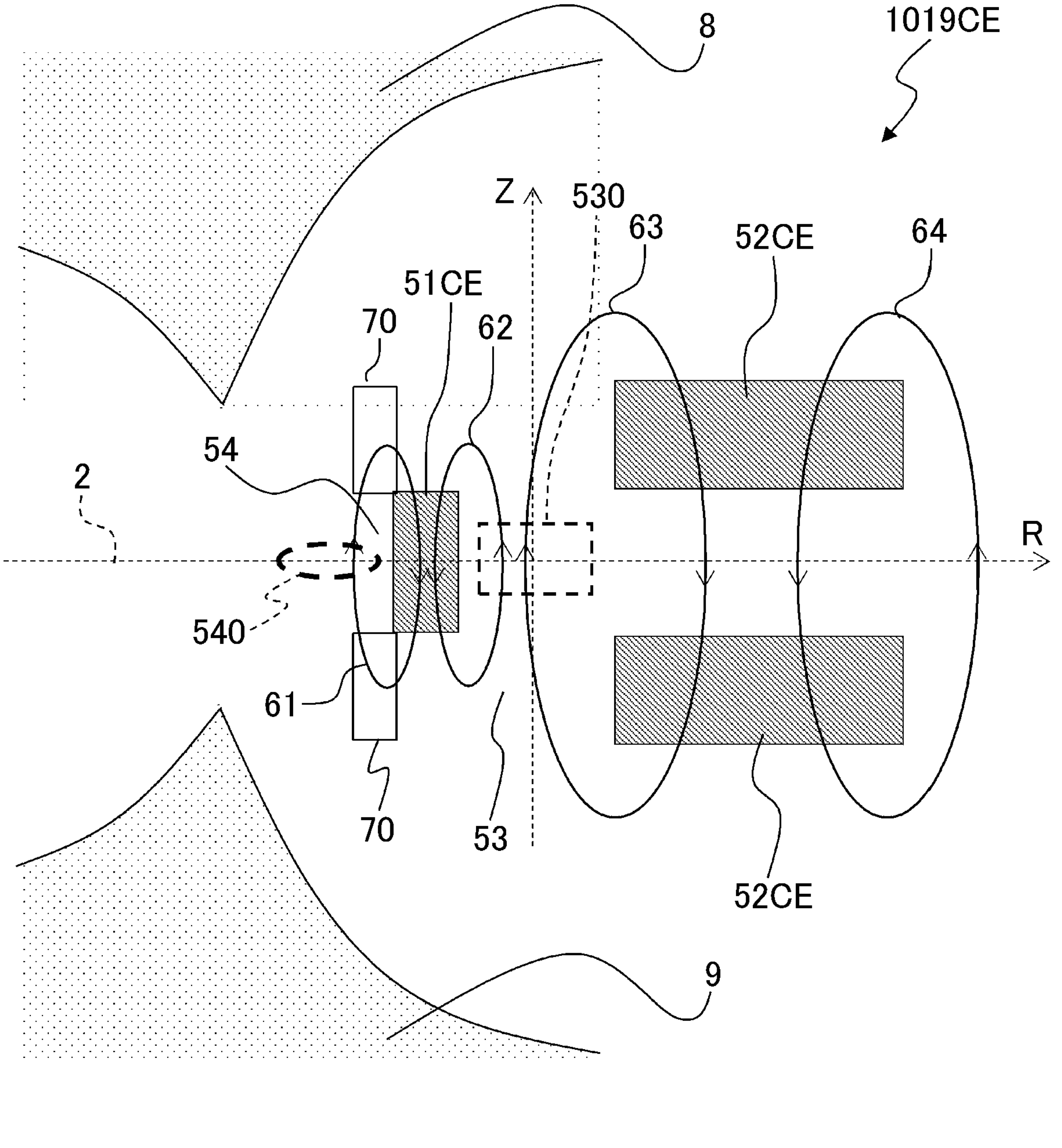
FIG. 17 is an explanatory view schematically illustrating a cross section of a magnetic channel of a comparative example.
Figure 18:
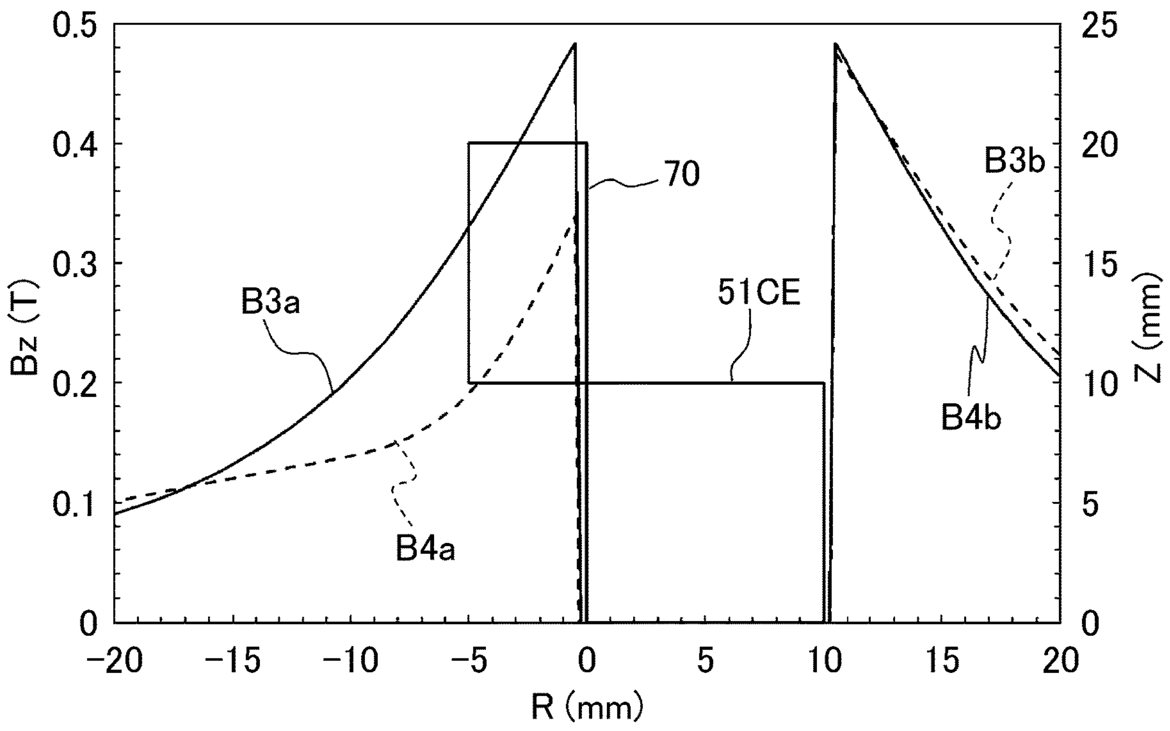
FIG. 18 is an explanatory view illustrating a magnetic field in the vicinity of a septum of the comparative example.
Figure 19:
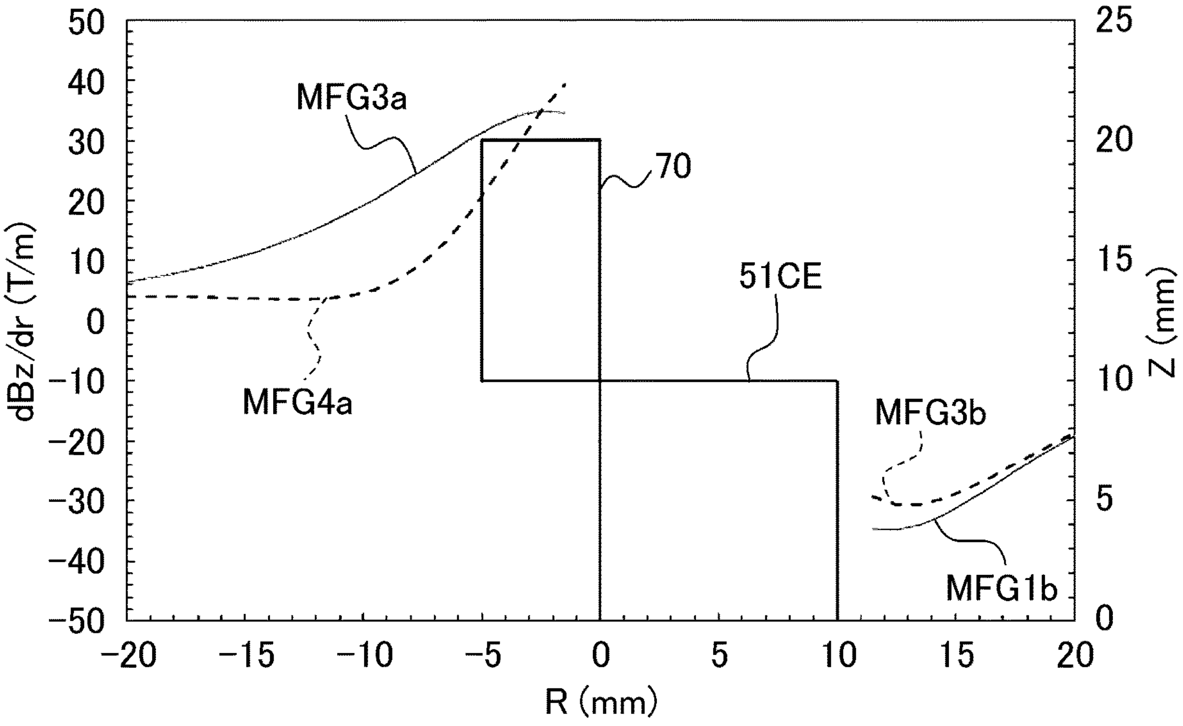
FIG. 19 is an explanatory view illustrating a magnetic field gradient in the vicinity of the septum of the comparative example.

FIGS. 17 to 19 are explanatory views of a comparative example of the present embodiment. The comparative example illustrated in FIGS. 17 to 19 is not described as the related art, but is described in order to describe the superiority of the operational effect of the present embodiment.

A septum 51CE of a comparative example illustrated in FIG. 17 is provide with iron members (hereinafter, referred to as correction iron pieces) 70 for magnetic field correction on the radially inner side thereof with an interval in the axial direction. Magnetic fields generated in the correction iron pieces suppress a magnetic field generated in the septum 51CE. When FIG. 17 is compared with FIGS. 13 and 14, an axial interval dimension between the correction iron pieces 70 is larger than the axial height dimension L2 (FIG. 14) of the circulating beam 540.

FIG. 18 illustrates a magnetic field in the vicinity of the radially inner side of the septum 51CE of the comparative example. A magnetic field B4*a* in a case where the correction iron pieces 70 are provided in the septum 51CE is slightly lower than a magnetic field B3*a* in a case where the correction iron pieces 70 are not provided in the septum 51CE. However, when FIG. 18 is compared with FIG. 15, the magnetic field B2*a* of the septum 51A having the recessed part 510A is lower than the magnetic field B4*a* of the septum 51CE having the correction iron pieces 70.

When attention is paid to the magnetic field on the radially outer side of the septum, a magnetic field B3*b* of the septum 51CE having the correction iron pieces 70 is slightly higher than a magnetic field B4*b* in the case where the correction iron pieces 70 are not provided. On the other hand, in the present embodiment illustrated in FIG. 15, the magnetic field B2*b* of the septum 51A having the recessed part 510A is lower than the magnetic field B1*b* in the case where the recessed part 510A is not provided.

FIG. 19 illustrates a magnetic field gradient in the vicinity of the septum 51CE of the comparative example. A magnetic field gradient MFG4*a* of the septum 51CE having the correction iron pieces 70 is slightly smaller than a magnetic field gradient MFG3*a* in the case where the correction iron pieces 70 are not provided, but the magnetic field gradient MFG3*a* increases as approaching the radially inner side of the septum 51CE. On the other hand, in the present embodiment illustrated in FIG. 16, the magnetic field gradient MFG2*a* of the septum 51A having the recessed part 510A is significantly smaller than the magnetic field gradient MFG1*a* in the case where the recessed part 510A is not provided, and decreases as approaching the radially inner side of the septum 51A.

When attention is paid to the magnetic field gradient on the radially outer side of the septum, a magnetic field gradient MFG3*b* of the septum 51CE having the correction iron pieces 70 is slightly larger than the magnetic field gradient MFG1*b* in the case where the correction iron pieces 70 are not provided. The same also applies to the case of the present embodiment illustrated in FIG. 16.

According to the present embodiment configured in this manner, it is unnecessary to provide the correction iron pieces 70 on the inner side of the septum, it is possible to suppress the magnetic field gradient in the vicinity of the septum 51 in the circulating beam region 54 only by forming the recessed part 510 in the septum 51, and it is possible to prevent a height dimension (height dimension along the axial direction of the main magnetic field magnet 1) of the circulating beam in the vertical direction from being limited, and to improve the beam extraction efficiency.

The above-described embodiment of the present disclosure is an example for describing the present disclosure, and is not intended to limit the scope of the present disclosure only to the embodiment. Those skilled in the art can practice the present disclosure in various other aspects without departing from the scope of the present disclosure.

What is claimed is:

1. An accelerator that accelerates an ion beam while circulating the ion beam by a main magnetic field and an accelerating radiofrequency electric field, the accelerator comprising:

a main magnetic field magnet that has a plurality of magnetic poles arranged to face each other and excites the main magnetic field in a space interposed between the magnetic poles;

a magnetic channel that extracts the ion beam from an inside of the main magnetic field magnet toward an outside of the main magnetic field magnet; and a displacement unit that displaces the ion beam circulating in a main magnetic field region where the main magnetic field is excited to an outer side of the main magnetic field region, wherein a disturbance magnetic field region is provided in an outer peripheral portion of the main magnetic field region, wherein a magnetic field which disturbs the ion beam displaced to the outer side and guides the ion beam to the magnetic channel is excited in the disturbance magnetic field region, wherein the magnetic channel includes a predetermined mechanism that suppresses a magnetic field gradient generated radially inward in a circulating ion beam region, wherein the magnetic channel includes a septum located on a radially inner side of the main magnetic field magnet and an anti-septum located on a radially outer side with a beam extraction passage interposed between the anti-septum and the septum, and wherein the predetermined mechanism is achieved by setting a radial width dimension of the septum to be smaller than a radial width dimension of the anti-septum, and setting a radial width dimension of a predetermined region where a median plane, orthogonal to an axial middle of the main magnetic field magnet, intersects with the septum to minimum.

2. A particle therapy system comprising the accelerator according to claim 1.

3. An accelerator that accelerates an ion beam while circulating the ion beam by a main magnetic field and an accelerating radiofrequency electric field, the accelerator comprising:

a main magnetic field magnet that has a plurality of magnetic poles arranged to face each other and excites the main magnetic field in a space interposed between the magnetic poles;

a magnetic channel that extracts the ion beam from an inside of the main magnetic field magnet toward an outside of the main magnetic field magnet; and a displacement unit that displaces the ion beam circulating in a main magnetic field region where the main magnetic field is excited to an outer side of the main magnetic field region, wherein a disturbance magnetic field region is provided in an outer peripheral portion of the main magnetic field region, wherein a magnetic field which disturbs the ion beam displaced to the outer side and guides the ion beam to the magnetic channel is excited in the disturbance magnetic field region, wherein the magnetic channel includes a predetermined mechanism that suppresses a magnetic field gradient generated radially inward in a circulating ion beam region, wherein the magnetic channel includes a septum located on a radially inner side of the main magnetic field magnet and an anti-septum located on a radially outer side with a beam extraction passage interposed between the anti-septum and the septum, and wherein the predetermined mechanism is achieved by forming a recessed part in a predetermined region where a median plane, orthogonal to an axial middle of the main magnetic field magnet, intersects with the septum.

4. The accelerator according to claim 3, wherein the recessed part is formed over a predetermined length range from a position corresponding to an inlet side of the beam extraction passage.

5. The accelerator according to claim 3, wherein a traverse section of the recessed part is formed to spread from a bottom center of the recessed part toward an opening side.

6. A particle therapy system comprising the accelerator according to claim 3.

7. An accelerator that accelerates an ion beam while circulating the ion beam by a main magnetic field and an accelerating radiofrequency electric field, the accelerator comprising:

a main magnetic field magnet that has a plurality of magnetic poles arranged to face each other and excites the main magnetic field in a space interposed between the magnetic poles;

a magnetic channel that extracts the ion beam from an inside of the main magnetic field magnet toward an outside of the main magnetic field magnet; and a displacement unit that displaces the ion beam circulating in a main magnetic field region where the main magnetic field is excited to an outer side of the main magnetic field region, wherein a disturbance magnetic field region is provided in an outer peripheral portion of the main magnetic field region, wherein a magnetic field which disturbs the ion beam displaced to the outer side and guides the ion beam to the magnetic channel is excited in the disturbance magnetic field region, wherein the magnetic channel includes a predetermined mechanism that suppresses a magnetic field gradient generated radially inward in a circulating ion beam region, wherein the magnetic channel includes a septum located on a radially inner side of the main magnetic field magnet and an anti-septum located on a radially outer side with a beam extraction passage interposed between the anti-septum and the septum, and wherein the predetermined mechanism is achieved by setting a radial width dimension of the septum to be smaller than a radial width dimension of the anti-septum, and forming a recessed part in a predetermined region where a median plane, orthogonal to an axial middle of the main magnetic field magnet, intersects with the septum to set a radial width dimension of the septum to minimum.

8. A particle therapy system comprising the accelerator according to claim 7.

* * * * *